US006828110B2

(12) United States Patent
Lee et al.

(10) Patent No.: US 6,828,110 B2
(45) Date of Patent: Dec. 7, 2004

(54) **ASSAYS FOR DETECTION OF *BACILLUS ANTHRACIS***

(75) Inventors: Bruce A. Lee, San Diego, CA (US); Becky Mar Flores, San Diego, CA (US); Gunars E. Valkirs, Escondido, CA (US)

(73) Assignee: Biosite Incorporated, San Diego, CA (US)

( * ) Notice: Subject to any disclaimer, the term of this patent is extended or adjusted under 35 U.S.C. 154(b) by 118 days.

(21) Appl. No.: 09/754,947

(22) Filed: Jan. 4, 2001

(65) Prior Publication Data

US 2004/0170967 A1 Sep. 2, 2004

Related U.S. Application Data

(60) Provisional application No. 60/174,901, filed on Jan. 6, 2000.

(51) Int. Cl.[7] .......................... G01N 33/53; C12N 1/00; A61K 39/07; C12P 21/04; C07H 21/04

(52) U.S. Cl. ................................ 435/7.1; 435/4; 435/5; 435/6; 435/7; 435/7.2; 435/7.21; 435/7.22; 435/7.3; 435/7.32; 435/810; 435/7.94; 435/7.95; 435/69.7; 436/501; 436/518; 536/23.7; 424/246.1

(58) Field of Search ........................... 435/4.7, 7.1, 7.2, 435/7.21, 7.22, 7.32, 7.3, 810, 7.94, 7.95, 69.7; 436/5.1, 518; 424/246.1; 536/23.7

(56) References Cited

U.S. PATENT DOCUMENTS

| | | | |
|---|---|---|---|
| 4,391,904 A | * | 7/1983 | Litman et al. |
| 5,496,700 A | * | 3/1996 | Ligler et al. |
| 6,448,016 B1 | * | 9/2002 | Rastogi et al. |

OTHER PUBLICATIONS

Bruno, et al. "In vitro selection of DNA aptamers to anthrax spores with electrochemiluminescence detection"; *Biosensors & Bioelectronics* (1999) pp. 457–464 vol. 14.

Etienne–Toumelin, et al. "Characterization of the *Bacillus anthracis* S–Layer: Cloning and Sequencing of the Structural Gene", *Journal of Bacteriology* (1995) pp. 614–620 vol. 177. No. 3.

Farchaus, et al. "Purification and Characterization of the Major Surface Array Protein from the Avirulent *Bacillus anthracis* Delta Steme–1", *Journal of Bacteriology* (1995) pp. 2481–2489 vol. 177. No. 9.

Franz, et al. "Clinical Recognition and Management of Patients Exposed to Biological Warefare Agents", *JAMA* (1997) pp. 399–411 vol. 278, No. 5.

Graham, et al. "Enzyme–Linked Lectinosorbent Assay (ELLA) for Detecting *Bacillus anthracis*", *Eur. J. Clin. Microbiol.* (1984) pp. 210–212 vol. 3, No. 3.

Longchamp and Leighton "Molecular recognition specificity of *Bacillus anthracis* spore antibodies", *Journal of Applied Microbiology* (1999) pp. 248–249 vol. 87.

Mesnage, et al. "Molecular characterization of the *Bacillus anthracis* main S–layer component: evidence that it is the major cell–associated antigen", *Molecular Microbiology* (1997) pp. 1147–1155 vol. 23(6).

Mesnage, et al. "The Capsule and S–Layer: Two Independent and Yet Compatible Macromolecular Structures in *Ballicus anthracis*", *Journal of Bacteriology* (1998) pp. 52–58 vol. 180.

Phillips and Martin "Investigation of spore surface antigens in the genus *Bacillus* by the use of polyclonal antibodies in immunofluorescence tests", *Journal of Applied Bacteriology* (1988) pp. 47–55 vol. 64.

Phillips, et al. "Monoclonal antibodies against spore antigens of *Bacillus anthracis*", FEBS Microbiology Immunology (1988) pp. 169–178 vol. 47.

Yu, "Comparative studies of magnetic particle–based solid phase fluorogenic and electrochemiluminescent imunoassay", *Journal of Immunological Methods* (1998) pp. 1–8 vol. 218.

* cited by examiner

*Primary Examiner*—Lynette R. F. Smith
*Assistant Examiner*—Padma Baskar
(74) *Attorney, Agent, or Firm*—Townsend and Townsend and Crew LLP

(57) ABSTRACT

This invention provides novel methods, reagents, and kits that are useful for detecting *B. anthracis*. The methods are based on the discovery of binding agents, including recombinant polyclonal antibodies, which bind to the surface array protein of *B. anthracis*.

28 Claims, No Drawings

ASSAYS FOR DETECTION OF *BACILLUS ANTHRACIS*

CROSS REFERENCE TO RELATED APPLICATION

The present application claims benefit of priority from U.S. Provisional Patent Application No. 60/174,901, filed Jan. 6, 2000, which is incorporated by reference.

BACKGROUND OF THE INVENTION

1. Field of the Invention

This invention pertains to the field of assays for detecting *Bacillus anthracis*, the causative agent of anthrax.

2. Background

Anthrax spores were first produced as weapons in the 1950s. Several countries including the former Soviet Union, the United States and Iraq are known to have produced anthrax weapons. Anthrax is a particularly fearsome biological warfare agent, not only because of its deadliness, but also because anthrax weapons are relatively easy to produce and deliver. Production of anthrax spores requires little more than basic laboratory equipment and growth media. Anthrax weapons are comprised of an anthrax source and an industrial sprayer that can produce aerosol particles of the appropriate size for victims to inhale. Such sprayers, for instance, can be mounted on low flying airplanes or other vehicles and used to spread anthrax over a wide area. Because of the ease and relatively small expense involved in producing and delivering anthrax weapons, such weapons are potentially highly attractive weapons of mass destruction for terrorist groups. Thus, in addition to potential organized military conflicts that may give rise to the use of such weapons, terrorist organizations are a potential threat for the use of such weapons in airports, office buildings and other centers of human activity.

Anthrax is caused by *Bacillus anthracis*, a gram-positive, sporulating bacillus. *B. anthracis* is a soil bacterium and is distributed worldwide. The organism exists in the infected host as a vegetative bacillus and in the environment as a spore. The anthrax spore is typically the infective form of the bacteria life cycle. Anthrax spores can survive adverse environmental conditions and can remain viable for decades. Animals such as cattle, sheep, goats and horses can contract the spores while grazing. Humans can contract anthrax from inoculation of minor skin lesions with spores from infected animals, their hides, wool or other products, such as infected meat (Franz et al. (1997) *J. Am. Med. Assoc*. 278(5): 399–411).

The typical mode of entry of the anthrax spore into the body, inhalation, results in an illness known as woolsorter's disease. After deposit in the lower respiratory tract, spores are phagocytized by tissue macrophages and transported to hilar and mediastinal lymph nodes. The spores germinate into vegetative bacilli, producing a necrotizing hemorrhagic mediastinitis (Franz et al., supra). Symptoms include fever, malaise and fatigue, which can easily be confused with the flu. The disease may progress to an abrupt onset of severe respiratory distress with dyspnea, stridor, diaphoresis and cyanosis. Death usually follows within 24 to 36 hours.

Because the effects of exposure to anthrax are not immediate, and because the initial symptoms are easily confused with the flu, there is a need for a fast method to detect *B. anthracis* in an environment where *B. anthracis* may have been released. This need is enhanced by the increasing number of anthrax threats that are called into governmental authorities each year. A fast method for determining whether public places have been exposed to anthrax spores in therefore essential.

Anthrax spores have S-layers, as do spores of many other archea and bacteria. Most S-layers are comprised of repeats of a single protein (Etienne-Toumelin et al., *J. Bacteriol.* 177:614–20 (1995)). The S-layer of *B. anthracis*, however, is comprised of at least two proteins: EA1 (Mesnage et al., *Molec. Microbiol.* 23:1147–55 (1997)) and surface array protein (SAP) (see Etienne-Toumelin, et al., supra). Fully virulent *B. anthracis* isolates are encapsulated by a capsule that encompasses the S-layer of the bacteria and prevents access of antibodies to both EA1 and SAP (Mesnage et al., *J. Bacteriol.* 180:52–58 (1998)).

Several methods for detecting *B. anthracis* have been reported, although none are optimal for quick and reliable detection of anthrax contamination. Detection methods include those based on amplification of nucleic acids that are specific for *B. anthracis* (Lee, *J. Appl. Microbiol.* 87:218–23 (1999); Patra, G., *FEMS Immunol. Med. Microbiol.* 15:223–31 (1996); Ramisse et al, *FEMS Microbiol. Lett.* 145(1):9–15 (1996); Bruno and Keil, *Biosens. Bioelectron.* 14:457–64 (1999); and Japanese Patent Nos. 11004693; 6261759; 6253847; and 6253846). The need to conduct time-consuming laboratory procedures to use these amplification methods limits their usefulness for quick identification of anthrax contamination. Other detection methods involve detecting spore-based epitopes of *B. anthracis* using antibodies (Yu, H., *J. Immunol. Methods* 218:1–8 (1998); Phillips et al., *J. Appl. Bacteriol.* 64:47–55 (1988); Phillips et al., *FEMS Microbiol. Immunol.* 1:169–78 (1988)). Other reported detection methods include an enzyme-linked lectinosorbent assay (Graham et al., *Eur. J. Clin. Microbiol.* 3:210–2 (1984)) and a method using DNA aptamers that bind anthrax spores (Bruno et al., *Biosens Bioelectron.* 14(5):457–64 (1999)).

Previous antibody-based detection methods for *B. anthracis* employed antibodies raised against whole anthrax spores. Such immunogens lead to the production of antibodies that cross-react with other related bacterial species. Longchamps et al., for instance, found that no antibody analyzed in their study was completely specific in recognizing anthrax spores (*J. Applied Microbiology* 87:246–49 (1999)). At least one study has shown that polyclonal antibodies raised against *B. anthracis* whole spore suspensions do not react with SAP protein (Mesnage et al, *Molec. Microbial.* 23:1147–55 (1997)). Closely related bacteria that may cross react with non-specific antibodies include *B. cereus, B. thuringiensis* and *B. mycoides* (Longchamp et al., supra.; Phillips et al., *FEMS Microbiol. Immunol.* 47:169–78 (1988)). This high degree of cross-reactivity is highly problematic for detection of anthrax because these non-toxic cross-reactive strains are widespread. *B. thuringiensis* in particular is commonly found in the soil, in part because the bacteria is sprayed on crops for its insecticidal qualities.

Therefore, a need exists for improved methods for detecting *Bacillus anthracis* in the environment. Such methods should be not only provide rapid results, but also should have little or no cross-reactivity with related species that are prevalent in nature. The present invention fulfills this and other needs.

SUMMARY OF THE INVENTION

The present invention provides novel methods of detecting *Bacillus anthracis*. The methods involve contacting a test sample with a capture reagent that can bind to *B.*

*anthracis* surface array protein (SAP), wherein the capture reagent forms a complex with SAP if SAP is present in the test sample, and detecting whether SAP is bound to the capture reagent. The capture reagent, for instance, can form a complex with the surface array protein if the surface array protein is present in the sample. Presence of the surface array protein is indicative of the presence of *B. anthracis* in the sample. In one embodiment, SAP comprises a polypeptide with the amino acid sequence shown in SEQ ID NO:1. In another embodiment, the *B. anthracis* strain is encapsulated.

The capture reagent can comprise an antibody that binds to SAP. In some embodiments, the antibody can be a recombinant antibody, such as a recombinant polyclonal or monoclonal antibody.

In a preferred embodiment, the test sample is collected from a site of suspected or threatened anthrax contamination. In another preferred embodiment, the test sample is collected using a cyclonic device. The test sample does not need to be cultured prior to contacting with the capture reagent.

In some methods of the invention, the capture reagent can be immobilized on a solid surface, such as a microtiter dish. The capture reagent can be immobilized on the solid support prior to contacting the capture reagent with the test sample.

In presently preferred embodiments, the assay methods of the invention are highly sensitive. For instance, in one embodiment, antibodies of the invention used according to the methods of the invention can detect *B. anthracis* at concentrations at least as low as 10,000 cfu/ml. In a more preferred embodiment, the methods of the invention are capable of detecting *B. anthracis* at concentrations at least as low as 5,000 cfu/ml. In still more preferred embodiments, the methods of the invention are capable of detecting *B. anthracis* at concentrations at least as low as 1,800 cfu/ml.

In some embodiments, SAP is detected by contacting SAP with a detection reagent that can bind SAP. Like the capture reagent, the detection reagent can be an antibody that binds SAP. For instance, the detection reagent can bind a different epitope of SAP than the capture agent binds. In some embodiments, the detection reagent comprises a detectable label. The detectable label can be, for instance, a radioactive label, a fluorophore, a dye, an enzyme or a chemilumunescent label.

The invention also provides devices and kits for detecting *B. anthracis*. The kits typically include, inter alia, a solid support upon which is immobilized a capture reagent which binds to a SAP of *B. anthracis*, and a detection reagent which binds to the SAP. In some embodiments the solid support is a microtiter dish. In another embodiment, the capture reagent is an antibody, such as a recombinant polyclonal or monoclonal antibody or mixtures thereof. The kit can also include written instructions for using the kit to determine whether a test sample contains *B. anthracis*. In some embodiments, the kit also comprises a positive control that comprises a polypeptide that comprises an antigenic determinant of *B. anthracis* SAP. The SAP can be, for example, the amino acid sequence displayed in SEQ ID NO:1.

The invention also provides for recombinant polyclonal antibody preparations that specifically bind to an antigenic determinant of *B. anthracis* SAP. For instance, the SAP polypeptide can be the amino acid sequence displayed in SEQ ID NO:1.

DETAILED DESCRIPTION

Definitions

The phrase "capture reagent" refers to a molecule that specifically binds to a specific target molecule. For instance, the target molecule can be a surface array protein (SAP) of *Bacillus anthracis*, or a portion thereof. Capture reagents include antibodies as well as naturally and non-naturally-occurring molecules that can specifically bind a target molecule. For instance, peptides that specifically bind a target molecule and are developed using phage display or other combinatorial system are encompassed by this definition.

A "test sample" is a sample obtained from a non-laboratory source that is not known to contain *B. anthracis*. For example, a sample grown on laboratory growth media or purified from laboratory growth media is not a test sample unless it is not known whether the sample contains *B. anthracis*.

The phrases "specifically binds to" or "specifically immnunoreactive with", when referring to an antibody or other binding moiety refers to a binding reaction which is determinative of the presence of a target antigen in the presence of a heterogeneous population of proteins and other biologics. Thus, under designated assay conditions, the specified binding moieties bind preferentially to a particular target antigen and do not bind in a significant amount to other components present in a test sample. Specific binding to a target antigen under such conditions may require a binding moiety that is selected for its specificity for a particular target antigen. A variety of immunoassay formats may be used to select antibodies that are specifically immunoreactive with a particular protein. For example, solid-phase ELISA immunoassays are routinely used to select monoclonal antibodies specifically immunoreactive with an antigen. See Harlow and Lane (1988) *Antibodies, A Laboratory Manual*, Cold Spring Harbor Publications, New York, for a description of immunoassay formats and conditions that can be used to determine specific immunoreactive. Typically a specific or selective reaction will be at least twice background signal or noise and more typically more than 10 to 100 times background. Specific binding between an antibody or other binding agent and an antigen generally means a binding affinity of at least $10^6$ $M^{-1}$. Preferred binding agents bind with affinities of at least about $10^7$ $M^{-1}$, and preferably $10^8$ $M^{-1}$ to $10^9$ $M^{-1}$ or $10^{10}$ $M^{-1}$.

The term "epitope" means an antigenic determinant that is capable of specific binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents. Epitopes can include non-contiguous amino acids, as well as contiguous amino acids.

The basic antibody structural unit is known to comprise a tetramer. Each tetramer is composed of two identical pairs of polypeptide chains, each pair having one "light" (about 25 kDa) and one "heavy" chain (about 50–70 kDa). The amino-terminal portion of each chain includes a variable region of about 100 to 110 or more amino acids primarily responsible for antigen recognition. The carboxy-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 more amino acids. (See generally, *Fundamental Immunology* (See, e.g., Paul, *Fundamental Immunology*, $3^{rd}$ Ed., 1993, Raven Press, New York).

The variable regions of each light/heavy chain pair form the antibody binding site. The chains all exhibit the same general structure of relatively conserved framework regions (FR) joined by three hypervariable regions, also called complementarily determining regions or CDRs. The CDRs from the two chains of each pair are aligned by the framework regions, enabling binding to a specific epitope. CDR and FR residues are delineated according to the standard sequence definition of Kabat et al., supra. An alternative structural definition has been proposed by Chothia et al. (1987) *J. Mol. Biol.* 196: 901–917; (1989) *Nature* 342: 878–883; and (1989) *J. Mol. Biol.* 186: 651–663.

The term "antibody" is used to mean whole antibodies and binding fragments thereof. Binding fragments include single chain fragments, Fv fragments and Fab fragments The term Fab fragment is sometimes used in the art to mean the binding fragments and Fab fragments from papain cleavage of an intact antibody. The terms Fab' and $F(ab')_2$ are sometimes used in the art to refer to binding fragments of intact antibodies generated by pepsin cleavage. Here, "Fab" is used to refer generically to double chain binding fragments of intact antibodies having at least substantially complete light and heavy chain variable domains sufficient for antigen-specific bindings, and parts of the light and heavy chain constant regions sufficient to maintain association of the light and heavy chains. Usually, Fab fragments are formed by complexing a full-length or substantially full-length light chain with a heavy chain comprising the variable domain and at least the CH1 domain of the constant region.

An "isolated" species or population of species means an object species (e.g., binding polypeptides of the invention) that is the predominant species present (i.e., on a molar basis it is more abundant than other species in the composition). Preferably, an isolated species comprises at least about 50, 80 or 90 percent (on a molar basis) of all macromolecular species present. Most preferably, the object species is purified to essential homogeneity (contaminant species cannot be detected in the composition by conventional detection methods).

The terms "identical" or percent "identity," in the context of two or more nucleic acids or polypeptide sequences, refer to two or more sequences or subsequences that are the same or have a specified percentage of nucleotides or amino acid residues that are the same, when compared and aligned for maximum correspondence, as measured using one of the following sequence comparison algorithms or by visual inspection.

The phrase "substantially identical," in the context of two nucleic acids, refers to two or more sequences or subsequences that have at least 80%, preferably 85%, most preferably 90–95% nucleotide identity, when compared and aligned for maximum correspondence, as measured using one of the following sequence comparison algorithms or by visual inspection. For amino acid sequences, "substantially identical" refers to two or more sequences or subsequences that have at least 60% identity, preferably 75% identity, and more preferably 90–95% identify, when compared and aligned for maximum correspondence, as measured using one of the following sequence comparison algorithms or by visual inspection. Preferably, the substantial identity exists over a region of the nucleic acid or amino acid sequences that is at least about 10 residues in length, more preferably over a region of at least about 20 residues, and most preferably the sequences are substantially identical over at least about 100 residues. In a most preferred embodiment, the sequences are substantially identical over the entire length of the specified regions (e.g., coding regions).

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) *J. Mol. Biol.* 215: 403–410 and Altschuel et al. (1977) *Nucleic Acids Res.* 25: 3389–3402, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

A further indication that two nucleic acids or polypeptides are substantially identical is that the polypeptide encoded by the first nucleic acid is immunologically cross-reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

"Conservatively modified variations" of a particular polynucleotide sequence refers to those polynucleotides that encode identical or essentially identical amino acid sequences, or where the polynucleotide does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent substitutions" or "silent variations," which are one species of "conservatively modified variations." Every polynucleotide sequence described herein which encodes a polypeptide also describes every possible silent variation, except where otherwise noted. Thus, silent substitutions are an implied feature of every nucleic acid sequence which encodes an amino acid. One of skill will recognize that each codon in a nucleic acid (except AUG, which is ordinarily the only codon for methionine and UGG, the only codon for tryptophan) can be modified to yield a functionally identical molecule by standard techniques. In some embodiments, the nucleotide sequences that encode the enzymes are preferably optimized for expression in a particular host cell (e.g., yeast, mammalian, plant, fungal, and the like) used to produce the enzymes.

Similarly, "conservative amino acid substitutions," in one or a few amino acids in an amino acid sequence are substituted with different amino acids with highly similar properties are also readily identified as being highly similar to a particular amino acid sequence, or to a particular nucleic acid sequence which encodes an amino acid. Such conservatively substituted variations of any particular sequence are a feature of the present invention. Individual substitutions, deletions or additions which alter, add or delete a single amino acid or a small percentage of amino acids (typically less than 5%, more typically less than 1%) in an encoded sequence are "conservatively modified variations" where the alterations result in the substitution of an amino acid with a chemically similar amino acid. Conservative substitution tables providing functionally similar amino acids are well known in the art. See, e.g., Creighton (1984) *Proteins*, W.H. Freeman and Company.

Description of the Preferred Embodiments

The present invention provides novel kits and methods for detecting the presence or absence of *B. anthracis* in a test sample. The kits and methods are a rapid, accurate and cost-effective means for detecting *B. anthracis*. The methods involve, in presently preferred embodiments, contacting a test sample with a capture reagent that can bind to *B. anthracis* SAP. The capture reagent then forms a complex with the SAP if it is present in the sample. The SAP is then detected to determine whether the test sample contains *B. anthracis*. Typically, detection is accomplished using a detection reagent that specifically binds to *B. anthracis* SAP. Both capture reagents and the detection reagents typically use binding moieties that can bind to SAP.

Unlike previously available anthrax detection methods, the methods and kits of the invention are highly sensitive. The assays and kits, in presently preferred embodiments, can detect *B. anthracis* when present in a sample at a concentration of about $10^4$ cfu/ml or less. Preferably, the detection limit for *B. anthracis* will be about $5\times10^3$ cfu/ml or less, more preferably about $1.8\times10^3$ cfu/ml or less, and still more preferably about $10^3$ cfu/ml or less.

Moreover, the methods and kits are highly specific for *B. anthracis*. Unlike previously available methods, the methods and kits of the present invention do not suffer from cross-reactivity with non-anthrax microorganisms. Previous methods of detecting *B. anthracis* relied on antibodies raised against whole anthrax spores, so these assays suffer from significant cross-reactivity. In contrast, the assays of the present invention use binding reagents that are directed to a *B. anthracis* antigen that is specific for *B. anthracis*. This antigen is secreted and can be deposited on the surface of anthrax spores and other particles, for example, during the preparation of anthrax-based biological weapons. Thus, in addition to the high specificity of the detection methods of the invention, the methods are more efficient and easy to use because there is no need to disrupt the anthrax spores for binding reagents to bind their antigens. Nor must samples suspected of containing *B. anthracis* be cultured prior to testing.

A. Binding Moieties that Specifically Bind *B. anthracis* Surface Array Protein The assays of the invention involve detecting the presence in a test sample of a *B. anthracis* SAP polypeptide, which is an antigen that is specific for *B. anthracis*. The assays for detecting SAP are, in some embodiments, binding assays. In these assays, which include immunoassays, SAP is immobilized on a solid support using a capture reagent that can specifically bind to SAP. The immobilized SAP is then detected using detection reagents that also are capable of specifically binding to SAP. The detection reagents typically include at least a binding moiety and a detectable label.

The invention provides binding reagents that are capable of specifically binding to the SAP antigen. These binding reagents can be used in one or more steps of the assay. For example, the binding reagents can be immobilized on a solid support and used to immobilize SAP on the solid support; such immobilized binding reagents are referred to herein as "capture reagents." Binding reagents can also be used to detect *B. anthracis* antigens by, for example, attaching a detectable label to a binding moiety that binds to SAP. Suitable binding moieties include any molecule that is capable of specifically binding to SAP. Antibodies and fragments thereof are examples of binding components that are suitable for use in detection moieties.

1. Types of Binding Moieties

The invention provides binding moieties (or reagents) that can specifically bind *B. anthracis* SAP polypeptides. Binding reagents can also be, for example, antibodies prepared using as immunogens natural, recombinant or synthetic polypeptides derived from *B. anthracis* SAP. The amino acid sequence of a *B. anthracis* SAP is shown as SEQ ID NO:1. Such polypeptides can function as immunogens that can be used for the production of monoclonal or polyclonal antibodies. Immunogenic peptides derived from SAP can also be used as immunogens; such peptides are sometimes conjugated to a carrier polypeptide prior to inoculation. Naturally occurring, recombinantly produced, or synthetic peptides or polypeptides are suitable for use as imnmunogens. These can be used in either pure or impure form. Production of antibodies against SAP polypeptides of the invention is discussed in more detail below. Suitable binding moieties also include those that are obtained using methods such as phage display.

Various procedures known in the art can be used for the production of antibodies that specifically bind to SAP. For the production of polyclonal antibodies, one can use SAP to inoculate any of various host animals, including but not limited to rabbits, mice, rats, sheep, goats, and the like. The SAP polypeptide can be prepared by recombinant means as described above using an expression vector containing a nucleic acid that encodes the *B. anthracis* SAP. For example, a nucleotide sequence encoding a *B. anthracis* SAP beginning at approximately 30 amino acids from the published N-terminus (i.e., at the presumed cleavage sequence) is presented in SEQ ID NO:2.

Monoclonal antibodies can be prepared by any technique that provides for the production of antibody molecules by continuous cell lines in culture, including the hybridoma technique originally developed by Kohler and Milstein ((1975) *Nature* 256: 495–497), as well as the trioma technique, the human B-cell hybridoma technique (Kozbor et al. (1983) *Immunology Today* 4: 72), and the EBV-hybridoma technique to produce human monoclonal antibodies (Cole et al. (1985) in *Monoclonal Antibodies and Cancer Therapy*, Alan R. Liss, Inc., pp. 77–96). Monoclonal antibodies also can be produced in germ-free animals as was described in PCT/US89/02545 (Publication No. WO8912690, published Dec. 12, 1989) and U.S. Pat. No. 5,091,512.

Fragments of antibodies are also useful as binding moieties. While various antibody fragments can be obtained by the digestion of an intact antibody, one of skill will appreciate that such fragments may be synthesized de novo either chemically or by utilizing recombinant DNA methodology. Thus, the term "antibody," as used herein, also includes antibody fragments either produced by the modification of whole antibodies or those synthesized de novo using recombinant DNA methodologies (e.g., single chain Fv). Single chain antibodies are also useful to construct detection moieties. Methods for producing single chain antibodies were described in, for example, U.S. Pat. No. 4,946,778. Techniques for the construction of Fab expression libraries were described by Huse et al. (1989) *Science* 246: 1275–1281; these techniques facilitate rapid identification of monoclonal Fab fragments with the desired specificity for SAP. Suitable binding moieties also include those that are obtained using methods such as phage display.

To prepare a suitable antigen preparation, one can prepare an expression library from *B. anthracis* and screen the library with a polyclonal antibody that is raised against a crude preparation of SAP. The inserts from those expression plasmids that express the SAP are then subcloned and sequenced. The SAP-encoding inserts are cloned into an expression vector and used to transform *E. coli* or other suitable host cells. The resulting preparation of recombinant SAP is then used to inoculate an animal, e.g., a mouse.

In preferred embodiments, the binding reagents are recombinantly produced polyclonal or monoclonal antibodies that bind to SAP. Recombinant antibodies are typically produced by immunizing an animal with SAP, obtaining RNA from the spleen or other antibody-expressing tissue of the animal, making cDNA, amplifying the variable domains of the heavy and light imnmunoglobulin chains, cloning the amplified DNA into a phage display vector, infecting *E. coli*, expressing the phage display library, and selecting those library members that express an antibody that binds to SAP. Methods suitable for carrying out each of these steps are described in, for example U.S. patent application Ser. No. 08/835,159, filed Apr. 4, 1997. In preferred embodiments, the antibody or other binding peptides are expressed on the cell surface of a replicable genetic unit, such as a filamentous phage, and especially phage M13, Fd and F1. Most work has inserted libraries encoding polypeptides to be displayed with either pIII or pVIII of these phage, forming a fusion protein which is displayed on the surface of the phage. See, e.g., Dower, WO 91/19818; Devlin, WO 91/18989; MacCafferty, WO 92/01047 (gene III); Huse, WO 92/06204; Kang, WO 92/18619 (gene VIII).

In a preferred embodiment, the genes that encode the heavy and light chains of antibodies present in the cDNA library are amplified using a set of primers that can amplify substantially all of the different heavy and light chains. The resulting amplified fragments that result from the amplification step are pooled and subjected to asymmetric PCR so that only one strand (e.g., the antisense strand) is amplified. The single strand products are phosphorylated, annealed to a single-stranded uracil template (e.g., the vector BS45, described in U.S. patent application Ser. No. 08/835,159, which has coding regions for the constant regions of mouse heavy and light chains), and introduced into a uracil DNA glycosylase$^+$ host cell to enrich for vectors that contain the coding sequences for heavy and light chain variable domains.

To screen for phage that express an antibody that binds to SAP, one can attach a label to SAP using methods known to those of skill in the art. In a preferred embodiment, the phage that display such antibodies are selected using SAP to which is attached an immobilizable tag, e.g., biotin. The phage are contacted with the biotinylated antigen, after which the phage are selected by contacting the resulting complex with avidin attached to a magnetic latex bead or other solid support. The selected phage are then plated, and may be screened with SAP to which is attached a detectable label.

In a preferred embodiment, the library is enriched for those phage that display more than one antibody that binds to SAP. Methods and vectors that are useful for this enrichment are described in U.S. patent application Ser. No. 08/835,159. The panning can be repeated one or more times to enhance the specificity and sensitivity of the resulting antibodies. Preferably, panning is continued until the percentage of functional positives is at least about 70%, more preferably at least about 80%, and most preferably at least about 90%.

A recombinant anti-SAP monoclonal antibody can then be selected by amplifying antibody-encoding DNA from individual plaques, cloning the amplified DNA into an expression vector, and expressing the antibody in a suitable host cell (e.g., *E. coli*). The antibodies are then tested for ability to bind SAP.

Recombinant polyclonal antibodies are particularly preferred because of the various forms of SAP that may be found in clinical samples due to, for example, proteolysis. The diverse fine binding specificity of members of a population of polyclonal antibodies often allows the population to bind to several forms of SAP (e.g., species variants, escape mutant forms, proteolytic fragments) to which a monoclonal reagent may be unable to bind. Methods for producing recombinant polyclonal antibodies are described in U.S. patent application Ser. No. 08/835,159, filed Apr. 4, 1997. Specific methods of producing recombinant polyclonal antibodies that bind to SAP are described in the Examples below.

Polyclonal antibodies can be prepared as described above, except that an individual antibody is not selected. Rather, the pool of phage is used for the screening, preferably using an equal number of phage from each sample. In preferred embodiments, the phage are enriched for those that display more than one copy of the respective antibodies. The phage are then selected for those that bind to SAP. For example, one can use a biotinylated anti-SAP monoclonal antibody and SAP to concentrate those phage that express antibodies that bind to SAP. The biotinylated monoclonal antibody is immobilized on a solid support (e.g., magnetic latex) to which is attached avidin. The phage that are bound to the immobilized SAP are eluted, plated, and the panning repeated until the desired percentage of functional positives is obtained.

2. Detection Reagents of the Invention

The presence of SAP is generally detected using a detection reagent that is composed of a binding moiety that specifically binds to SAP. Suitable binding moieties are discussed above. The detection reagents are either directly labeled, i.e., comprise or react to produce a detectable label, or are indirectly labeled, i.e., bind to a molecule that is itself labeled with a detectable label. Labels can be directly attached to or incorporated into the detection reagent by chemical or recombinant methods.

In one embodiment, a label is coupled to a molecule, such as an antibody that specifically binds to SAP, through a chemical linker. Linker domains are typically polypeptide sequences, such as poly-gly sequences of between about 5 and 200 amino acids. In some embodiments, proline residues are incorporated into the linker to prevent the formation of significant secondary structural elements by the linker. Preferred linkers are often flexible amino acid subsequences that are synthesized as part of a recombinant fusion protein comprising the RNA recognition domain. In one embodiment, the flexible linker is an amino acid subsequence that includes a proline, such as Gly(x)-Pro-Gly(x) (SEQ ID NO:5) where x is a number between about 3 and about 100. In other embodiments, a chemical linker is used to connect synthetically or recombinantly produced recognition and labeling domain subsequences. Such flexible linkers are known to persons of skill in the art. For example, poly(ethylene glycol) linkers are available from Shearwater Polymers, Inc. Huntsville, Ala. These linkers optionally have amide linkages, sulfhydryl linkages, or heterofinctional linkages.

The detectable labels used in the assays of the present invention, which are attached to the detection reagent, can be primary labels (where the label comprises an element that is detected directly or that produces a directly detectable element) or secondary labels (where the detected label binds to a primary label, e.g., as is common in immunological labeling). An introduction to labels, labeling procedures and detection of labels is found in Polak and Van Noorden (1997) *Introduction to Immunocytochemistry*, 2nd ed., Springer Verlag, N.Y. and in Haugland (1996) *Handbook of Fluorescent Probes and Research Chemicals*, a combined handbook and catalogue Published by Molecular Probes, Inc., Eugene, Oreg. Patents that described the use of such labels include U.S. Pat. Nos. 3,817,837; 3,850,752; 3,939,350; 3,996,345; 4,277,437; 4,275,149; and 4,366,241.

Primary and secondary labels can include undetected elements as well as detected elements. Useful primary and secondary labels in the present invention can include spectral labels such as green fluorescent protein, fluorescent dyes (e.g., fluorescein and derivatives such as fluorescein isothiocyanate (FITC) and Oregon Green™, rhodamine and derivatives (e.g., Texas red, tetrarhodimine isothiocynate (TRITC), etc.), digoxigenin, biotin, phycoerythrin, AMCA, CyDyes™, and the like), radiolabels (e.g., $^3H$, $^{125}I$, $^{35}S$, $^{14}C$, $^{32}P$, 33P, etc.), enzymes (e.g., horse radish peroxidase, alkaline phosphatase etc.), spectral colorimetric labels such as colloidal gold or colored glass or plastic (e.g. polystyrene, polypropylene, latex, etc.) beads. The label can be coupled directly or indirectly to a component of the detection assay (e.g., the detection reagent) according to methods well known in the art. As indicated above, a wide variety of labels may be used, with the choice of label depending on sensitivity required, ease of conjugation with the compound, stability requirements, available instrumentation, and disposal provisions.

Preferred labels include those that use: 1) chemiluminescence (using horseradish peroxidase and/or alkaline phosphatase with substrates that produce photons as breakdown products as described above) with kits being available, e.g., from Molecular Probes, Amersham, Boehringer-Mannheim, and Life Technologies/Gibco BRL; 2) color production (using both horseradish peroxidase and/or alkaline phosphatase with substrates that produce a colored product (kits available from Life Technologies/Gibco BRL, and Boehringer-Mannheim)); 3) fluorescence using, e.g., an enzyme such as alkaline phosphatase, together with the substrate AttoPhos (Amersham) or other substrates that produce fluorescent products, 4) fluorescence (e.g., using Cy-5 (Amersham), fluorescein, and other fluorescent tags); 5) radioactivity. Other methods for labeling and detection will be readily apparent to one skilled in the art.

For use of the present invention outside the laboratory, preferred labels are non-radioactive and readily detected without the necessity of sophisticated instrumentation. Preferably, detection of the labels will yield a visible signal that is immediately discernable upon visual inspection. One preferred example of detectable secondary labeling strategies uses an antibody that recognizes SAP in which the antibody is linked to an enzyme (typically by recombinant or covalent chemical bonding). The antibody is detected when the enzyme reacts with its substrate, producing a detectable product. Preferred enzymes that can be conjugated to detection reagents of the invention include, e.g., β-galactosidase, luciferase, horse radish peroxidase, and alkaline phosphatase. The chemiluminescent substrate for luciferase is luciferin. One embodiment of a fluorescent substrate for β-galactosidase is 4-methylumbelliferyl-β-D-galactoside. Embodiments of alkaline phosphatase substrates include p-nitrophenyl phosphate (pNPP), which is detected with a spectrophotometer; 5-bromo-4-chloro-3-indolyl phosphate/nitro blue tetrazoliuum (BCIP/NBT) and fast red/napthol AS-TR phosphate, which are detected visually; and 4-methoxy-4-(3-phosphonophenyl) spiro[1,2-dioxetane-3,2'-adamantane], which is detected with a luminometer. Embodiments of horse radish peroxidase substrates include 2,2'azino-bis(3-ethylbenzthiazoline-6 sulfonic acid) (ABTS), 5-aminosalicylic acid (5 AS), o-dianisidine, and o-phenylenediarnine (OPD), which are detected with a spectrophotometer; and 3,3,5,5'-tetramethylbenzidine (TMB), 3,3'diaminobenzidine (DAB), 3-amino-9-ethylcarbazole (AEC), and 4-chloro-1-naphthol (4C1N, which are detected visually. Other suitable substrates are known to those skilled in the art. The enzyme-substrate reaction and product detection are performed according to standard procedures known to those skilled in the art and kits for performing enzyme immunoassays are available as described above.

The presence of a label can be detected by inspection, or a detector which monitors a particular probe or probe combination can be used to detect the detection reagent label. Typical detectors include spectrophotometers, phototubes and photodiodes, microscopes, scintillation counters, cameras, film and the like, as well as combinations thereof. Examples of suitable detectors are widely available from a variety of commercial sources known to persons of skill. Commonly, an optical image of a substrate comprising bound labeling moieties is digitized for subsequent computer analysis.

B. *B. anthracis* Protein Surface Array Protein (SAP) Nucleic Acids and Polypeptides The binding reagents used in the assays and kits of the invention are generally obtained using a *B. anthracis* SAP polypeptide as an immunogen. The entire SAP can be used, or polypeptide subfragments that include an immunogenic epitope can be used. Suitable SAP immunogens can be isolated from *B. anthracis* cultures, or more preferably can be produced using recombinant methods.

1. SAP Polypeptides

SAP polypeptides can be produced by methods known to those of skill in the art. The amino acid sequence of a *B. anthracis* SAP polypeptide is provided as SEQ ID NO:1. A *B. anthracis* SAP polypeptide from a different strain is described in Etienne-Toumelin et al., *J. Bacteriol.* 177:614–620 (1995).

In a presently preferred embodiment, the SAP proteins, or immunogenic subsequences thereof, are synthesized using recombinant DNA methodology. Generally this involves creating a DNA sequence that encodes the polypeptide, modified as desired, placing the DNA in an expression cassette under the control of a particular promoter, expressing the protein in a host, isolating the expressed protein and, if required, renaturing the protein.

SAP polypeptides can be expressed in a variety of host cells, including *E. coli*, other bacterial hosts, yeasts, filamentous fungi, and various higher eukaryotic cells such as the COS, CHO and HeLa cells lines and myeloma cell lines. Techniques for gene expression in microorganisms are described in, for example, Smith, *Gene Expression in Recombinant Microorganisms* (*Bioprocess Technology*, Vol. 22), Marcel Dekker, 1994. Examples of bacteria that are useful for expression include, but are not limited to, Escherichia, Enterobacter, Azotobacter, Erwinia, Bacillus, Pseudomonas, Klebsielia, Proteus, Salmonella, Serratia, Shigella, Rhizobia, Vitreoscilla, and Paracoccus. Filamentous fungi that are useful as expression hosts include, for example, the following genera: Aspergillus, Trichoderma, Neurospora, Penicillium, Cephalosporium, Achlya, Podospora, Mucor, Cochliobolus, and Pyricularia. See, e.g., U.S. Pat. No. 5,679,543 and Stahl and Tudzynski, Eds., *Molecular Biology in Filamentous Fungi*, John Wiley & Sons, 1992. Synthesis of heterologous proteins in yeast is well known and described in the literature. *Methods in Yeast Genetics*, Sherman, F., et al., Cold Spring Harbor Laboratory, (1982) is a well recognized work describing the various methods available to produce the enzymes in yeast.

SAP proteins, whether recombinantly or naturally produced, can be purified, either partially or substantially to homogeneity, according to standard procedures of the art, such as, for example, ammonium sulfate precipitation, affinity columns, column chromatography, gel electrophoresis and the like (see, generally, R. Scopes, *Protein Purification*, Springer-Verlag, N.Y. (1982), Deutscher, *Methods in Enzymology* Vol 182*: Guide to Protein Purification*., Academic Press, Inc. N.Y. (1990)). Once purified, partially or to homogeneity as desired, the polypeptides can then be used (e.g., as immunogens for antibody production).

One of skill in the art would recognize that after chemical synthesis, biological expression, or purification, the SAP protein(s) may possess a conformation substantially different than the native conformations of the constituent polypeptides. In this case, it may be necessary or desirable to denature and reduce the polypeptide and then to cause the polypeptide to re-fold into the preferred conformation. Methods of reducing and denaturing proteins and inducing re-folding are well known to those of skill in the art (See, Debinski et al. (1993) *J. Biol. Chem.* 268: 14065–14070; Kreitman and Pastan (1993) *Bioconjug. Chem.* 4: 581–585; and Buchner et al. (1992) *Anal. Biochem.* 205: 263–270). Debinski et al., for example, describe the denaturation and reduction of inclusion body proteins in guanidine-DTE. The protein is then refolded in a redox buffer containing oxidized glutathione and L-arginine.

One of skill also would recognize that modifications can be made to the SAP polypeptides without diminishing their immunogenic activity. Some modifications can be made to facilitate the cloning, expression, or incorporation of the polypeptide into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

2. *B. anthracis* SAP-encoding Nucleic Acids

Nucleic acids that encode *B. anthracis* are useful for the recombinant production of SAP. Such nucleic acids can be isolated, for example, by routine cloning methods. The cDNA sequence provided in SEQ ID NO:2 can be used to provide probes that specifically hybridize to a SAP gene, to a SAP mRNA, or to a SAP cDNA in a cDNA library (e.g., in a Southern or Northern blot). Once the target SAP nucleic acid is identified, it can be isolated according to standard methods known to those of skill in the art (see, e.g., Sambrook, Berger, and Ausubel, supra.).

SAP nucleic acids also can be isolated by amplification methods such as polyrnerase chain reaction (PCR), the ligase chain reaction (LCR), the tnanscription-based amplification system (TAS), the self-sustained sequence replication system (SSR). A wide variety of cloning and in vitro amplification methodologies are well-known to persons of skill. Examples of these techniques and instructions sufficient to direct persons of skill through many cloning exercises are found in Berger, Sambrook, and Ausubel (all supra.); Cashion et al., U.S. Pat. No. 5,017,478; and Carr, European Patent No. 0,246,864. Examples of techniques sufficient to direct persons of skill through in vitro amplification methods are found in Berger, Sambrook, and Ausubel, as well as Mullis et al. (1987) U.S. Pat. No. 4,683,202*; PCR Protocols A Guide to Methods and Applications* (Innis et al., eds) Academic Press Inc. San Diego, Calif. (1990) (Innis); Arnheim & Levinson (Oct. 1, 1990) *C&EN* 36–47*; The Journal Of NIH Research* (1991) 3: 81–94; (Kwoh et aL (1989) *Proc. Nat'l. Acad. Sci. USA* 86: 1173; Guatelli et al. (1990) *Proc. Natl. Acad. Sci. USA* 87: 1874; Lomell et al. (1989) *J. Clin. Chem.* 35: 1826; Landegren et al. (1988) *Science* 241: 1077–1080; Van Brunt (1990) *Biotechnology* 8: 291–294; Wu and Wallace (1989) *Gene*, 4: 560; and Barringer et al. (1990) *Gene* 89: 117.

A polynucleotide that encodes a SAP polypeptide can be operably linked to appropriate expression control sequences for a particular host cell in which the polypeptide is to be expressed. Such constructs are often referred to as "expression cassettes." For *E. coli*, appropriate control sequences include a promoter such as the T7, trp, or lambda promoters, a ribosome binding site and preferably a transcription termination signal. For eukaryotic cells, the control sequences typically include a promoter which optionally includes an enhancer derived from immunoglobulin genes, SV40, cytomegalovirus, etc., and a polyadenylation sequence, and may include splice donor and acceptor sequences. In yeast, convenient promoters include GAL1,10 (Johnson and Davies (1984) *Mol. Cell. Biol.* 4:1440–1448) ADH2 (Russell et al. (1983) *J. Biol. Chem.* 258:2674–2682), PHO5 (*EMBO J.* (1982) 6:675–680), and MFα1 (Herskowitz and Oshima (1982) in *The Molecular Biology of the Yeast Saccharomyces* (eds. Strathern, Jones, and Broach) Cold Spring Harbor Lab., Cold Spring Harbor, N.Y., pp. 181–209).

Expression cassettes are typically introduced into a vector that facilitates entry into a host cell, and maintenance of the expression cassette in the host cell. Vectors that include a polynucleotide that encodes a SAP polypeptide are provided by the invention. Such vectors often include an expression cassette that can drive expression of the SAP polypeptide. To easily obtain a vector of the invention, one can clone a polynucleotide that encodes the SAP polypeptide into a commercially or commonly available vector. A variety of common vectors suitable for this purpose are well known in the art. For cloning in bacteria, common vectors include pBR322 derived vectors such as pBLUESCRIPT™, and λ-phage derived vectors. In yeast, vectors include Yeast Integrating plasmids (e.g., YIp5) and Yeast Replicating plasmids (the YRp series plasmids) and pGPD-2. A multi-copy plasmid with selective markers such as Leu-2, URA-3, Trp-1, and His-3 is also commonly used. A number of yeast expression plasmids such as YEp6, YEp13, YEp4 can be used as expression vectors. The above-mentioned plasmids have been fuilly described in the literature (Botstein et al. (1979) *Gene* 8:17–24; Broach et al. (1979) *Gene*, 8:121–133). For a discussion of yeast expression plasmids, see, e.g., Parents, B., *YEAST* (1985), and Ausubel, Sambrook, and Berger, all supra). Expression in mammalian cells can be achieved using a variety of commonly available plasmids, including pSV2, pBC12BI, and p9103, as well as lytic virus vectors (e.g., vaccinia virus, adenovirus, and baculovirus), episomal virus vectors (e.g., bovine papillomavirus), and retroviral vectors (e.g., murine retroviruses).

The nucleic acids that encode SAP polypeptides can be transferred into the chosen host cell by well-known methods such as calcium chloride transformation for *E. coli* and calcium phosphate treatment or electroporation for *E. coli* or mammalian cells. Cells transformed by the plasmids can be selected by resistance to antibiotics conferred by genes contained on the plasmids, such as the amp, gpt, neo and hyg genes, among others. Techniques for transforming fungi are well known in the literature and have been described, for instance, by Beggs et al. ((1978) *Proc. Natl. Acad. Sci. USA* 75: 1929–1933), Yelton et al. ((1984) *Proc. Natl. Acad. Sci. USA* 81: 1740–1747), and Russell ((1983) *Nature* 301: 167–169). Procedures for transforming yeast are also well known (see, e.g., Beggs (1978) *Nature* (London), 275:104–109; and Hinnen et al. (1978) *Proc. Natl. Acad. Sci. USA*, 75:1929–1933. Transformation and infection methods for mammalian and other cells are described in Berger and Kimmel, *Guide to Molecular Cloning Techniques, Methods in Enzymology* 152 Academic Press, Inc., San Diego, Calif. (Berger); Sambrook et al. (1989) *Molecular Cloning—A Laboratory Manual* (2nd ed.) Vol. 1–3, Cold Spring Harbor Laboratory, Cold Spring Harbor Press, NY, (Sambrook et al.); *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel).

C. Assay Formats

The *B. anthracis* detection methods of the present invention can be carried out in a wide variety of assay formats. Typically, the assay methods involve immobilization of *B. anthracis* SAP on a solid support, followed by detection of the inmnobilized SAP. The detectable labels can be detected directly after immobilization on the solid support, for example, or indirectly by an enzymatic or other reaction that results in a detectable change in a reactant that is present in the detection assay reaction.

1. ELISA Detection Methods of the Invention

Presently preferred assay systems for use in the kit and methods of the invention are based on the enzyme-linked immunosorbent assay (ELISA) method. General methods for ELISA are well known to those of skill in the art (see, e.g., Elder et al., *J. Clin. Microbiol.* 16:141 (1982); Ausubel et al., supra). Generally, antigens fixed to a solid surface are detected using antigen-specific antibodies that are detected by way of an enzymatic reaction. In a presently preferred embodiment, the ELISA method used is the "sandwich" method wherein the antigens are bound to the solid surface via an antibody bound to the solid surface. A second antibody, typically linked to an enzyme, is then contacted to the antigen, washed, then contacted with the enzyme substrate to select binding. These and other embodiments of the ELISA method are taught in, for example, Ausubel et al. § 11.2, supra.

To immobilize SAP on the solid support, a capture reagent that specifically binds to SAP is non-diffusively associated with the support. The capture reagents can be non-diffusively immobilized on the support either by covalent or non-covalent methods, which are known to those of skill in the art. See, e.g., Pluskal et al. (1986) *BioTechniques* 4: 272–283. Suitable supports include, for example, glasses, plastics, polymers, metals, metalloids, ceramics, organics, and the like. Specific examples include, but are not limited to, microtiter plates, nitrocellulose membranes, nylon membranes, and derivatized nylon membranes, beads, and also particles, such as agarose, SEPHADEX™, and the like. Assay systems for use in the methods and kits of the invention include, but are not limited to, dipstick-type devices, immunochromatographic test strips and radial partition immunoassay devices, microtiter assays and flow-through devices. Conveniently, where the solid support is a membrane, the test sample can flow through the membrane, for example, by gravity, capillary action, or under positive or negative pressure.

Once the test sample has been contacted with the solid support, the solid support is then contacted with detection reagents for SAP. The solid support can be washed prior to contact with detection reagents to remove unbound reagents and test sample components. After incubation of the detection reagents for a sufficient time to bind a substantial portion of the immobilized SAP, any unbound labeled reagents are removed by, for example, washing. The detectable label associated with the detection reagents is then detected. For example, in the case of an enzyme used as a detectable label, a substrate for the enzyme that turns a visible color upon action of the enzyme is placed in contact with the bound detection reagent. A visible color will then be observed in proportion to the amount of the specific antigen in the sample.

2. Membrane-based Detection Methods of the Invention

In some embodiments, the assay methods are carried out using a membrane-based detection system such as are described in U.S. Pat. No. 5,922,615 and EP 447154. These systems employ an apparatus that includes a porous member, such as a membrane or a filter, onto which is bound a multiplicity of capture reagents that specifically bind *B. anthracis* SAP. The apparatus also includes a non-absorbent member with a textured surface in communication with the lower surface of the porous member. The textured surface of the non-absorbent member can be a grooved surface (e.g., analogous to the surface of a record album) or it can be composed of channels, such that when the porous and non-absorbent members are brought into contact with one another a network of capillary channels is formed. The capillary network is formed from the contact of the porous member with the textured surface of the non-absorbent member and can be constructed either before or subsequent to the initial contacting of the porous member with a fluid.

In some embodiments, the capillary communication between the porous member and the non-absorbent member favors delaying the transferal of fluid from the porous member to the capillary network formed by the porous member and the textured surface of the non-absorbent member until the volume of the added fluid substantially exceeds the void volume of the porous member. The transferal of fluid from the porous member to the network of capillary channels formed by the porous member and the textured surface of the non-absorbent member can occur without the use of external means, such as positive external pressure or vacuum, or contact with an absorbent material.

The devices of the present invention can also include an optional member which is placed in contact with the upper surface of the porous member and may be used to partition the upper surface of the device into discrete openings. Such openings can access either the porous member or the textured surface of the non-absorbent second member. The optional member can in conjunction with the non-absorbent member compose a fluid receiving zone in which there is no intervening porous member. A fluid receiving zone constructed from the non-absorbent member and the optional member provides fluid capacity in addition to that provided by the network of capillary channels created by the contact of the porous member and the non-absorbent member. The openings in the optional member may include a first fluid opening and also an additional fluid opening. The first fluid opening functions as a portal for the introduction of the first fluid added to the device. The additional fluid opening serves as an additional portal through which additional fluids may be added to the inventive device.

To perform an assay using these devices, a volume of the test sample is added to the porous member, where the sample permeates the void volume of the porous member and thereby contacts the anchor moieties immobilized on the porous member. In a non-competitive assay, the sample to be assayed is applied to the porous member and the SAP, if present, is bound by the anchor moieties. A detection reagent for SAP is then added as an additional fluid; these bind to the complex of SAP and capture reagent. Alternatively, the detection reagent can be added to the sample prior to application of the sample to the porous member so that the binding of detection reagent to SAP occurs prior to the binding of SAP to the capture reagent. In another embodiment, the capture reagent and detection reagent are added to the sample, after which the complex of capture reagent, SAP, and detection reagent binds to a binding agent that is either combined with these reagents or is immobilized on the porous member. An additional fluid containing reagents to effect a separation of free from bound labeled reagents can be added to remove excess detection reagent, if needed.

This device is designed to provide sufficient sensitivity to measure low concentrations of SAP because one can use large amounts of sample and efficiently remove the excess of detection reagent. Indeed, the efficient separation of free from bound label achieved by the network of capillary channels of this device improves the discrimination of specific SAP-associated signal over non-specific background signal. If needed, a signal developer solution is then added to enable the label of the detection moiety to develop a detectable signal. The signal developed can then be related to the concentration of the target ligand within the sample. In a preferred embodiment, the transfer of fluid between the porous first member of the device and the network of capillary channels formed by the contact of the porous member and textured surface of the non-absorbent second member of the device is generally self-initiated at the point when the total volume of fluid added to the device exceeds the void volume of the porous member, thus obviating the need for active interaction by the user to remove excess fluid from the analyte detection zone. The point at which the fluid transfer is initiated is dependent upon the objectives of the assay. Normally, it is desirable to contact the sample with all of the zones on the porous member which contain immobilized receptor. This method enables the detection of SAP in a manner that is simple, rapid, convenient, sensitive and efficient in the use of reagents.

Competitive binding assays can also be used to detect SAP. Conveniently, these assays are performed using the described devices by adding to a sample a labeled analog of SAP. The labeled analog and SAP present in the sample compete for the binding sites of the capture reagents. Alternatively, the capture reagents can be combined with the sample and labeled analogs with subsequent immobilization of the capture reagents onto the porous member through contact with a binding agent. An additional fluid to separate the free from bound label may be added to the device, followed if needed by a signal development solution to enable detection of the label of the labeled analog which has complexed with capture reagent immobilized on the porous member. The amount of labeled SAP bound to the porous member is related to the concentration of SAP in the sample.

D. Kits for Detecting Anthrax

This invention also provides kits for the detection and/or quantification of anthrax using the methods described herein. T he kits can include a container containing one or more of the above-discussed detection reagents with or without labels, and capture reagents, either free or bound to solid supports. A suitable solid support, such as a membrane, can also be included in the kits of the invention. The kits can provide the solid supports in the form of an assay apparatus that is adapted to use in the described assay. Preferably, the kits will also include reagents used in the described assays, including reagents useful for detecting the presence of the detectable labels. Other materials useful in the performance of the assays can also be included in the kits, including test tubes, transfer pipettes, and the like. The kits can also include written instructions for the use of one or more of these reagents in any of the assays described herein.

The kits of the invention can also include an internal and/or an external control. An internal control can consist of the SAP polypeptide. The control antigen can conveniently be preattached to a capture reagent in a zone of the solid support adjacent to the zone to which the sample is applied. The external control can also consist of the SAP polypeptide. Typically, the antigen present in the external control will be at a concentration at or above the sensitivity limit of the assay means. The external control antigen can be diluted in the sample diluent and assayed in the same manner as would a biological sample. Alternatively, the external control SAP polypeptide can be added to an aliquot of an actual biological sample to determine the sensitivity of the assay. The kits of the present invention can contain materials sufficient for one assay, or can contain sufficient materials for multiple assays.

E. Test Samples

Samples to test for the presence of anthrax can be collected from any potential source of anthrax. Samples can be collected from, for example, the air, water, food, soil or other solids or liquids. In one embodiment, the methods and kits of the invention can be used to determine if terrorists have planted anthrax in a public area. In preferred embodiments, it is unknown whether the test sample contains *B. anthracis*.

Air samples can be collected using, for example, a cyclonic collection device (see, e.g., Jensen et al., *Am. Ind. Hyg. Assoc. J.* 53:660–67 (1992); Cage et al., *Ann. Allergy Asthma Immunol.* 77:401–6 (1996)). Such a device can capture a volume of air, submit the air to turbulence such that any particles in the air (e.g., anthrax spores or SAP-coated particles) are deposited on a moist surface. Typically, air flowing through cyclonic tubes forms a vortex in the tube that induces high centrifugal forces on particles in the air (Anderson et al., *Johns Hopkins APL Technical Digest* 20(3) (1999)). The rotational forces segregate the larger particle to the outside of the tube. Variations in the tube diameter, length, taper angle and flow velocity determine particle separation size. Particles can then be captured by letting the particles slide down the tube walls into a filter bag or by washing the walls with a liquid and capturing the concentrate. The objects can then be collected and analyzed for the presence of anthrax. A variety of cyclonic devices are discussed in, e.g., Maddox et al. *Monthly Microscopical J.* 286–290 (1870); Fisher-Klostertman, Inc. Product Bulletin 218-C, 2900 West Broadway, Louisville, Ky.; Hering, "Impactors, Cyclones, and Other Inertial and Gravitational Collectors," in *Air Sampling Instruments for Evaluation of Atmospheric contaminants*, 8th Ed., American Conference of Governmental Industrial Hygienists, Cincinnati, Ohio, 279–321 (1995) and; Stoutas, et al. *J. Aerosol Sci.* 25(7): 1321–1330 (1994). Handheld air samplers can also be used to obtain samples that are tested according to the methods of the invention (see, e.g., Kenny et al., *Am. Ind. Hyg. Assoc. J.* 59:831–41 (1998)). Sampling of solid or liquid objects is known to those skilled in the art.

Several cyclonic collection devices are known, including conventional impactors and virtual impactors. Conventional impactors work by directing the particle-containing air through a nozzle onto a collection plate. A variation of the conventional impactor is the virtual impactor, which operates by directing the air stream from the nozzle to an opening with a restricted flow. Larger particles enter an opening which forms a virtual surface, and become entrained in a minor flow or reduced velocity, while smaller particles follow the major flow. The virtual impactor has the benefit of concentrating particle quantity from low density in the high volume flow to high density in the low volume flow. See, e.g., Anderson et al., supra.

A significant advantage of the assay methods and kits of the invention is that the sensitivity is such that a sample need not be cultured prior to assay. This not only provides a faster and less expensive assay, but also makes it possible to obtain a result in the field. Samples need not be sent to a laboratory facility for processing. This is particularly advantageous in military situations, in which suitable laboratory facilities may not be available.

EXAMPLES

The following examples are offered to illustrate, but not to limit the present invention.

Example 1

Isolation of a Gene Encoding *Bacillus anthracis* Surface Array Protein (SAP)

This Example describes the cloning and characterization of a gene that encodes a *B. anthracis* surface array protein (SAP).

Isolation of *B. Anthracis* DNA

*B. anthracis* genomic DNA isolated from the non-pathologic Sterne strain was used as a template source for PCR amplification of a nucleic acid that codes for SAP. A total of 6 ml of *Bacillus anthracis* Sterne strain ($1\times10^{10}$/ml in PBS pH 7.4) was pelleted in a microcentrifuge at 10,000 g for 5 minutes. Bacterial pellets were then combined and resuspended in a final volume of 1 ml lysis buffer (50 mM Tris(hydroxymethyl) aminomethane ("Tris") pH 7.8, 10 mM ethylenediaminetetraacetic acid ("EDTA"), 100 μg/ml Ribonuclease (RNase A) (Roche Molecular Biochemical, Indianapolis, Ind.), 0.5% Triton X-100™ (T-octylphenoxypolyethoxyethanol) (Sigma, St. Louis, Mo.), 12.5% sucrose). Lysozyme (Sigma) was added to a final concentration of 2 mg/ml and the mixture incubated for 1 hr at 37° C. 300 μg of Proteinase K (Roche Molecular Biochemical, Indianapolis, Ind.) and a one-tenth volume of 10% SDS was added to the mixture followed by a 1 hr incubation at 56° C. NaCl was then added to a final concentration of 500 mM by adding one-tenth volume of 5 M NaCl. The mixture was then twice extracted with phenol/chloroform (phenol:chloroform:isoamyl alcohol (50:49:1)) and the DNA in the aqueous layer sheared by passing the solution through an 18 gauge needle. DNA was precipitated with 2.5 volumes of ethanol and resuspended in 200 μl of distilled water. This DNA preparation was extracted once with Tris pH 8 equilibrated phenol, two times with phenol/chloroform and finally twice with chloroform (chloroform:isoamyl alcohol (49:1)) alone. DNA in the aqueous layer was precipitated a final time and resuspended in 500 μl of distilled water, yielding approximately 79 μg of DNA at 158 μg/ml. This DNA was used as a template in the subsequent PCR amplification of the SAP gene.

Cloning of *Bacillus Anthracis* SAP Gene via PCR

Appropriate PCR primers were made corresponding to the coding sequence of the 5' and 3' ends of the *B. anthracis* SAP gene (see primer sequence below). These primers were based on a published nucleotide sequence (Etienne-Toumelin et al., supra). DNA encoding the native signal sequence of SAP (amino acids 1–29) was purposefully omitted from the cloning since a functional signal sequence was provided by the expression vector pBRncoH3 (described in copending, commonly-owned U.S. patent application Ser. No. 08/835,159, filed Apr. 4, 1997). The 5' primer contains 23 bases of vector sequence at its 5'-end that corresponds to the 3'-end of the pBRncoH3 vector. The 3' primer contains 19 bases of the tetracycline promoter, removed by HindIII digestion in the vector, in addition to 20 bases of vector sequence 3' to the HindIII site. The 3' primer was also engineered to encode a hexahistidine amino acid tag at the C-terminus of the SAP protein to allow for efficient purification using nickel-chelate affinity chromatography (see below).

5' PCR primer: 5'-TCGCTGCCCAACCAGCCATGGC-CGCAGGTAAAA CATTCCCAGAC-3' (SEQ ID NO:3)

3' PCR primer: 5'-GTGATAAACTACCGCATTAAA-GCTTATCGATGATA AGCTGTCAATTAGTGATG-GTGATGGTGATGTTTTG TTGCAGGTTTTGCTTCTTT-3' (SEQ ID NO:4)

The nucleic acid that encodes SAP was amplified using these primers and approximately 30 ng of *Bacillus anthracis* genomic DNA as template. The amplification was performed using Expand™ DNA polymerase (Roche Molecular Biochemical (Indianapolis, Ind.). SAP insert DNA (~300 ng) was purified and annealed to the HindIII-digested pBRncoH3 vector (100 ng) at a 6:1 molar ratio of insert to vector. An aliquot was electroporated into 40 μl of electrocompetent *E. coli* strain DH10B as described in Example 3. Various dilutions of the transformed cells were plated on LB agar plates supplemented with tetracycline (10 μg/ml) and grown overnight at 37° C. Three colonies were each picked into 3 ml 2×YT, supplemented with tetracycline (10 μgl/ml), and grown overnight at 37° C. The following day, glycerol freezer stocks were made for long term storage at −80° C.

In order to confirm that the SAP gene had indeed been cloned, each of the three clones was tested for the ability to synthesize SAP protein upon arabinose induction as described below. All three clones produced a protein of the predicted size, approximately 94 kDa in molecular mass, and were shown to react with a rabbit anti-anthracis polyclonal serwn using Western blot analysis (data not shown). Two of the three clones were sequenced and compared against the National Center for Biotechnology Information's (NCBI) non-redundant nucleotide database using the BLAST search engine. This search indicated that a SAP gene had indeed been cloned. There were eight differences in the predicted amino acid sequence compared to the noted published sequence. These changes are lysine 264 to arginine, glutamic acid 478 to alanine, arginine 482 to histidine, glutamic acid 496 to aspartic acid, lysine 556 to arginine, glutamic acid 606 to aspartic acid, lysine 607 to threonine, and valine 751 to alanine. Amino acid numbering is based on the published sequence (Etienne-Tournelin et al., supra). These differences may be due to the fact that a different *Bacillus anthracis* strain was used in the work described here. The original published work did not use the Sterne strain. The predicted amino acid sequence of the SAP gene cloned here shows 8 amino acid differences out of 785, and is thus 99.0% identical to the published sequence.

Example 2

Expression and Purification of Recombinant *Bacillus Anthracis* SAP from *E. coli*

This Example describes the expression and purification of *Bacillus anthracis* SAP using *E. coli.*

A shake flask containing 2×YT supplemented with 1% glycerol was inoculated with an *E. coli* DH10B strain from Example 1 that contained a cloned *B. anthracis* SAP gene and incubated overnight in an Innova 4330 incubator shaker (New Brunswick Scientific, Edison, N.J.) set at 37° C., 300 rpm. The inoculum was used to seed 500 mL cultures of defined medium (Pack et al. (1993) *Bio/Technology* 11: 1271–1277) supplemented with 3 g/L L-leucine, 3 g/L L-isoleucine, 12 g/L casein digest (Difco, Detroit, Mich.), 12.5 g/L glycerol and 10 μg/ml tetracycline. Cultures were grown in 2 L Tunair shake flasks (Shelton Scientific, Shelton, Conn.) at 37° C. and 300 rpm. Cells were grown to an optical density of approximately 4 absorption units at 600 nm. Expression of SAP was then induced by addition of L(+)-arabinose to 2 g/L during this logarithmic growth phase. The flasks were then maintained at 23° C. and 300 rpm overnight.

The following morning, bacterial cultures were passed through an M-110Y Microfluidizer (Microfluidics, Newton, Mass.) at 17,000 psi. The homogenate was clarified in a J2-21 centrifuge (Beckmnan, Fullerton, Calif.) and recombinant SAP purified from the supernatant using immobilized metal affinity chromatography. Briefly, Chelating Sepharose FastFlow™ resin (Pharmacia, Piscataway, N.J.) was charged with 0.1 M $NiCl_2$ and equilibrated in 20 mM borate, 150 mM NaCl, 10 mM imidazole, 0.01% $NaN_3$, pH 8. A stock solution was used to bring the supernatant concentration to 10 mM imidazole, pH 8. Chelating resin was then added to the supernatant and the mixture shaken for 1 hour at room temperature, 150–200 rpm. During this time, SAP was captured by means of the high affinity interaction between nickel and the hexahistidine tag engineered onto the C-terminus of SAP. After 1 hour, the resin mixture was poured into a chromatography column and washed with 20 mM borate, 150 mM NaCl, 10 mM imidazole, 0.01% $NaN_3$, pH 8.0. SAP was eluted from the resin with the same buffer containing 200 mM imidazole instead of 10 mM.

The volume of eluted SAP was reduced using a centrifuge concentrator with a 30 kDa molecular weight cut off (Amicon, Beverly, Mass.), and the sample subsequently dialyzed against sterile phosphate-buffered solution (PBS) for immunizations and BBS (20 mM borate, 150 mM NaCl, 0.01% $NaN_3$, pH 8.0) for biotinylation. Isolated SAP was evaluated for purity by SDS-PAGE analysis and shown to be greater than 95% pure. The protein concentration of recombinant SAP was determined by UV absorbance at 280 nm, assuming an absorbance of 0.593 for a 1 mg/ml solution.

Example 3

Construction of a Phage-display Library

This Example describes the construction of a phage display library from which binding reagents that are specific for *B. anthracis* SAP were identified.

Immunization and mRNA Isolation

A phage display library for identification of SAP-binding molecules was constructed as follows. A/J mice (Jackson Laboratories, Bar Harbor, Me.) were immunized intraperitoneally with recombinant SAP antigen, using 100 μg protein in Freund's complete adjuvant, on day 0, and with 100 μg antigen on day 28. Test bleeds of mice were obtained through puncture of the retro-orbital sinus. If, by testing the titers, they were deemed high by ELISA using biotinylated SAP antigen immobilized via neutravidin (Reacti-Bind# NeutrAvidin™-Coated Polystyrene Plates, Pierce, Rockford, Ill.), the mice were boosted with 100 μg of protein on day 70, 71 and 72, with subsequent sacrifice and splenectomy on day 77. If titers of antibody were not deemed satisfactory, mice were boosted with 100 μg antigen on day 56 and a test bleed taken on day 63. If satisfactory titers were obtained, the animals were boosted with 100 μg of antigen on day 98, 99, and 100 and the spleens harvested on day 105.

The spleens were harvested in a laminar flow hood and transferred to a petri dish, trimming off and discarding fat and connective tissue. The spleens were macerated quickly with the plunger from a sterile 5 cc syringe in the presence of 1.0 ml of solution D (25.0 g guanidine thiocyanate (Boehringer Mannheim, Indianapolis, Ind.), 29.3 ml sterile water, 1.76 ml 0.75 M sodium citrate pH 7.0, 2.64 ml 10% sarkosyl (Fisher Scientific, Pittsburgh, Pa.), 0.36 ml 2-mercaptoethanol (Fisher Scientific, Pittsburgh, Pa.)). This spleen suspension was pulled through an 18 gauge needle until all cells were lysed and the viscous solution was transferred to a microcentrifuge tube. The petri dish was washed with 100 $\mu$l of solution D to recover any remaining spleen. This suspension was then pulled through a 22 gauge needle an additional 5–10 times.

The sample was divided evenly between two microcentrifuge tubes and the following added, in order, with mixing by inversion after each addition: 50 $\mu$l 2 M sodium acetate pH 4.0, 0.5 ml water-saturated phenol (Fisher Scientific, Pittsburgh, Pa.), 100 $\mu$l chloroform/isoamyl alcohol 49:1 (Fisher Scientific, Pittsburgh, Pa.). The solution was vortexed for 10 seconds and incubated on ice for 15 min. Following centrifugation at 14 krpm for 20 min at 2–8° C., the aqueous phase was transferred to a fresh tube. An equal volume of water saturated phenol:chloroform:isoamyl alcohol (50:49:1) was added, and the tube vortexed for ten seconds. After a 15 min incubation on ice, the sample was centrifuged for 20 min at 2–8° C., and the aqueous phase transferred to a fresh tube and precipitated with an equal volume of isopropanol at −20°C. for a minimum of 30 min. Following centrifugation at 14 krpm for 20 min at 4° C., the supernatant was aspirated away, the tubes briefly spun and all traces of liquid removed from the RNA pellet.

The RNA pellets were each dissolved in 300 $\mu$l of solution D, combined, and precipitated with an equal volume of isopropanol at −20° C. for a minimum of 30 min. The sample was centrifuged 14 krpm for 20 min at 4° C., the supematant aspirated as before, and the sample rinsed with 100 $\mu$l of ice-cold 70% ethanol. The sample was again centrifuged 14 krpm for 20 min at 4° C., the 70% ethanol solution aspirated, and the RNA pellet dried in vacuo. The pellet was resuspended in 100 $\mu$l of sterile diethyl pyrocarbonate-treated water. The concentration was determined by $A_{260}$ using an absorbance of 1.0 for a concentration of 40 $\mu$g/ml. The RNAs were stored at −80° C.

Preparation of Complementary DNA (cDNA)

The total RNA purified from mouse spleens as described above was used directly as template for cDNA preparation. RNA (50 $\mu$g) was diluted to 100 $\mu$L with sterile water, and 10 $\mu$L of 130 ng/$\mu$L oligo $dT_{12}$ (synthesized on Applied Biosystems Model 392 DNA synthesizer) was added. The sample was heated for 10 min at 70° C., then cooled on ice. Forty $\mu$L 5× first strand buffer was added (Gibco/BRL, Gaithersburg, Md.), along with 20 $\mu$L 0.1 M dithiothreitol (Gibco/BRL, Gaithersburg, Md.), 10 $\mu$L 20 mM deoxynucleoside triphosphates (dNTP's, Boehringer Mannheim, Indianapolis, Ind.), and 10 $\mu$L water on ice.

The sample was then incubated at 37° C. for 2 min. Ten $\mu$L reverse transcriptase (Superscript™ II, Gibco/BRL, Gaithersburg, Md.) was added and incubation was continued at 37° C. for 1 hr. The cDNA products were used directly for polymerase chain reaction (PCR).

Amplification of Antibody Genes by PCR

To amplify substantially all of the H and L chain genes using PCR, primers were chosen that corresponded to substantially all published sequences. Because the nucleotide sequences of the amino termini of H and L contain considerable diversity, 33 oligonucleotides were synthesized to serve as 5' primers for the H chains, and 29 oligonucleotides were synthesized to serve as 5' primers for the kappa L chains as described in U.S. patent application Ser. No. 08/835,159, filed Apr. 4, 1997. The constant region nucleotide sequences for each chain required only one 3' primer for the H chains and one 3' primer for the kappa L chains.

A 50 $\mu$L reaction was performed for each primer pair with 50 pmol of 5' primer, 50 pmol of 3' primer, 0.25 $\mu$L Taq DNA Polymerase (5 units/$\mu$L, Boehringer Mannheim, Indianapolis, Ind.), 3 $\mu$L cDNA (prepared as described in Example 3), 5 $\mu$L 2 mM dNTP's, 5 $\mu$L 10×Taq DNA polymerase buffer with $MgCl_2$ (Boehringer Mannheim, Indianapolis, Ind.), and $H_2O$ to 50 $\mu$L. Amplification was done using a GeneAmp® 9600 thermal cycler (Perkin Elmer, Foster City, Calif.) with the following therrnocycle program: 94° C. for 1 min; 30 cycles of 94° C. for 20 sec, 55° C. for 30 sec, and 72° C. for 30 sec; 72° C. 6 min; 4° C.

The dsDNA products of the PCR process were then subjected to asymmetric PCR using only a 3' primer to generate substantially only the anti-sense strand of the target genes. A 100 $\mu$L reaction was done for each dsDNA product with 200 pmol of 3' primer, 2 $\mu$L of ds-DNA product, 0.5 $\mu$L Taq DNA Polymerase, 10 $\mu$L 2 mM dNTP's, 10 $\mu$L 10×Taq DNA polymerase buffer with $MgCl_2$ (Boehringer Mannheim, Indianapolis, Ind.), and $H_2O$ to 100 $\mu$L. The same PCR program as that described above was used to amplify the single-stranded (ss)-DNA.

Purification of Single-stranded DNA by High Performance Liquid Chromatography and Kinasing Single-stranded DNA The H chain ss-PCR products and the L chain single-stranded PCR products were ethanol precipitated by adding 2.5 volumes ethanol and 0.2 volumes 7.5 M ammonium acetate and incubating at −20° C. for at least 30 min. The DNA was pelleted by centrifuging in an Eppendorf centrifuge at 14 krpm for 10 min at 2–8° C. The supernatant was carefully aspirated, and the tubes were briefly spun a 2nd time. The last drop of supernatant was removed with a pipette. The DNA was dried in vacuo for 10 min on medium heat. The H chain products were pooled in 210 $\mu$L water and the L chain products were pooled separately in 210 $\mu$L water. The single-stranded DNA was purified by high performance liquid chromatography (HPLC) using a Hewlett Packard 1090 HPLC and a Gen-Pak™ FAX anion exchange column (Millipore Corp., Milford, Mass.). The gradient used to purify the single-stranded DNA is shown in Table 1, and the oven temperature was 60° C. Absorbance was monitored at 260 nm. The single-stranded DNA eluted from the HPLC was collected in 0.5 min fractions. Fractions containing single-stranded DNA were ethanol precipitated, pelleted and dried as described above. The dried DNA pellets were pooled in 200 $\mu$L sterile water.

TABLE 1

HPLC gradient for purification of ss-DNA

| Time (min) | % A | % B | % C | Flow (ml/min) |
|---|---|---|---|---|
| 0 | 70 | 30 | 0 | 0.75 |
| 2 | 40 | 60 | 0 | 0.75 |
| 17 | 15 | 85 | 0 | 0.75 |
| 18 | 0 | 100 | 0 | 0.75 |
| 23 | 0 | 100 | 0 | 0.75 |
| 24 | 0 | 0 | 100 | 0.75 |
| 28 | 0 | 0 | 100 | 0.75 |
| 29 | 0 | 100 | 0 | 0.75 |
| 34 | 0 | 100 | 0 | 0.75 |
| 35 | 70 | 30 | 0 | 0.75 |

Buffer A is 25 mM Tris, 1 mM EDTA, pH 8.0
Buffer B is 25 mM Tris, 1 mM EDTA, 1 M NaCl, pH 8.0
Buffer C is 40 mm phosphoric acid The single-stranded DNA was 5'-phosphorylated in preparation for mutagenesis. Twenty-four $\mu$L 10×kinase buffer (United States Biochemical, Cleveland, Ohio, 10.4 $\mu$L 10 mM adenosine-5'-triphosphate (Boehringer Mannheim, Indianapolis, Ind.), and 2 $\mu$L polynucleotide kinase (30 units/$\mu$L, United States Biochemical, Cleveland, Ohio) was added to each sample, and the tubes were incubated at 37°

C. for 1 hr. The reactions were stopped by incubating the tubes at 70° C. for 10 min. The DNA was purified with one extraction of Tris equilbrated phenol (pH>8.0, United States Biochemical, Cleveland, Ohio):chloroform:isoamyl alcohol (50:49:1) and one extraction with chloroform:isoamyl alcohol (49:1). After the extractions, the DNA was ethanol precipitated and pelleted as described above. The DNA pellets were dried, then dissolved in 50 $\mu$L sterile water. The concentration was determined by measuring the absorbance of an aliquot of the DNA at 260 nm using 33 $\mu$g/ml for an absorbance of 1.0. Samples were stored at −20° C.

Preparation of Uracil Templates used in Generation of Spleen Antibody Phage Libraries One ml of *E. coli* CJ236 (BioRAD, Hercules, Calif.) overnight culture was added to 50 ml 2×YT in a 250 ml baffled shake flask. The culture was grown at 37° C. to $OD_{600}$=0.6, inoculated with 10 $\mu$l of a 1/100 dilution of BS45 vector phage stock (described in U.S. patent application Ser. No. 08/835,159, filed Apr. 4, 1997) and growth continued for 6 hr. Approximately 40 ml of the culture was centrifuged at 12 krpm for 15 minutes at 4° C. The supernatant (30 ml) was transferred to a fresh centrifuge tube and incubated at room temperature for 15 minutes after the addition of 15 $\mu$l of 10 mg/ml RNaseA (Boehringer Mannheim, Indianapolis, Ind.). The phage were precipitated by the addition of 7.5 ml of 20% polyethylene glycol 8000 (Fisher Scientific, Pittsburgh, Pa.)/3.5M ammonium acetate (Sigma Chemical Co., St. Louis, Mo.) and incubation on ice for 30 min. The sample was centrifuged at 12 krpm for 15 min at 2–8° C. The supernatant was carefully discarded, and the tube briefly spun to remove all traces of supernatant. The pellet was resuspended in 400 $\mu$l of high salt buffer (300 mM NaCl, 100 mM Tris pH 8.0, 1 mM EDTA), and transferred to a 1.5 ml tube.

The phage stock was extracted repeatedly with an equal volume of equilibrated phenol:chloroform:isoamyl alcohol (50:49:1) until no trace of a white interface was visible, and then extracted with an equal volume of chloroform:isoamyl alcohol (49:1). The DNA was precipitated with 2.5 volumes of ethanol and 1/5 volume 7.5 M ammonium acetate and incubated 30 min at −20° C. The DNA was centrifuged at 14 krpm for 10 min at 4° C., the pellet washed once with cold 70% ethanol, and dried in vacuo. The uracil template DNA was dissolved in 30 $\mu$l sterile water and the concentration determined by $A_{260}$ using an absorbance of 1.0 for a concentration of 40 $\mu$g/ml. The template was diluted to 250 ng/$\mu$L with sterile water, aliquoted, and stored at −20° C.

Mutagenesis of Uracil Template with ss-DNA and Electroporation into *E. coli* to Generate Antibody Phage Libraries Antibody phage display libraries were generated by simultaneously introducing single-stranded heavy and light chain genes onto a phage display vector uracil template. A typical mutagenesis was performed on a 2 $\mu$g scale by mixing the following in a 0.2 ml PCR reaction tube: 8 $\mu$l of (250 ng/$\mu$L) uracil template, 8 $\mu$L of 10× annealing buffer (200 mM Tris pH 7.0, 20 mM $MgCl_2$, 500 mM NaCl), 3.33 $\mu$l of kinased single-stranded heavy chain insert (100 ng/$\mu$L), 3.1 $\mu$l of kinased single-stranded light chain insert (100 ng/$\mu$L), and sterile water to 80 $\mu$l. DNA was annealed in a GeneAmp™ 9600 thermal cycler using the following thermal profile: 20 sec at 94° C., 85° C. for 60 sec, 85° C. to 55° C. ramp over 30 min, hold at 55° C. for 15 min. The DNA was transferred to ice after the program finished. The extension/ligation was carried out by adding 8 $\mu$l of 10× synthesis buffer (5 mM each dNTP, 10 mM ATP, 100 mM Tris pH 7.4, 50 mM $MgCl_2$, 20 mM DTT), 8 $\mu$L T4 DNA ligase (1U/$\mu$L, Boehringer Mannheim, Indianapolis, Ind.), 8 $\mu$L diluted T7 DNA polymerase (1U/$\mu$L, New England Biolabs, Beverly, Mass.) and incubating at 37° C. for 30 min. The reaction was stopped with 300 $\mu$L of mutagenesis stop buffer (10 mM Tris pH 8.0, 10 mM EDTA). The mutagenesis DNA was extracted once with equilibrated phenol (pH>8):chloroform:isoamyl alcohol (50:49:1), once with chloroform:isoamyl alcohol (49:1), and the DNA was ethanol precipitated at −20° C. for at least 30 min. The DNA was pelleted and the supernatant carefully removed as described above. The sample was briefly spun again and all traces of ethanol removed with a pipetman. The pellet was dried in vacuo. The DNA was resuspended in 4 $\mu$L of sterile water.

One microliter of mutagenesis DNA (500 ng) was transferred into 40 $\mu$l electrocompetent *E. coli* DH12S (Gibco/BRL, Gaithersburg, Md.) using electroporation. The transformed cells were mixed with approximately 1.0 ml of overnight XL-1 cells which were diluted with 2×YT broth to 60% the original volume. This mixture was then transferred to a 15-ml sterile culture tube and 9 ml of top agar added for plating on a 150-mm LB agar plate. Plates were incubated for 4 hrs at 37° C. and then transferred to 20° C. overnight. First round antibody phage were made by eluting phage off these plates in 10 ml of 2×YT, spinning out debris, and taking the supernatant. These samples are the antibody phage display libraries used for selecting antibodies against SAP. Efficiency of the electroporations was measured by plating 10 $\mu$l of a $10^{-4}$ dilution of suspended cells on LB agar plates, follow by overnight incubation of plates at 37° C. The efficiency was calculated by multiplying the number of plaques on the $10^{-4}$ dilution plate by $10^6$. Library electroporation efficiencies are typically greater than $1\times10^7$ phage under these conditions.

Transformation of *E. coli* by Electroporation

Electrocompetent *E. coli* cells were thawed on ice. DNA was mixed with 40 $\mu$L of these cells by gently pipetting the cells up and down 2–3 times, being careful not to introduce an air bubble. The cells were transferred to a Gene Pulser cuvette (0.2 cm gap, BioRAD, Hercules, Calif.) that had been cooled on ice, again being careful not to introduce an air bubble in the transfer. The cuvette was placed in the *E. coli* Pulser (BioRAD, Hercules, Calif.) and electroporated with the voltage set at 1.88 kV according to the manufacturer's recommendation. The transformed sample was immediately resuspended in 1 ml of 2×YT broth or 1 ml of a mixture of 400 $\mu$l 2×YT/600 $\mu$l overnight XL-1 cells and processed as procedures dictated.

Plating M13 Phage or Cells Transformed with Antibody Phage-display Vector Mutagenesis Reaction Phage samples were added to 200 $\mu$L of an overnight culture of *E. coli* XL1-Blue when plating on 100 mm LB agar plates or to 600 $\mu$L of overnight cells when plating on 150 mm plates in sterile 15 ml culture tubes. After adding LB top agar (3 ml for 100 mm plates or 9 ml for 150 mm plates, top agar stored at 55° C. (see, Appendix A1, Sambrook et al., supra.), the mixture was evenly distributed on an LB agar plate that had been pre-warmed (37° C.–55° C.) to remove any excess moisture on the agar surface. The plates were cooled at room temperature until the top agar solidified. The plates were inverted and incubated at 37° C. as indicated.

Preparation of Biotinylated SAP and Biotinylated Antibodies

Concentrated recombinant SAP antigen (Example 2 above) was extensively dialyzed into BBS (20 mM borate, 150 mM NaCl, 0.1% $NaN_3$, pH 8.0). After dialysis, 1 mg of SAP (1 mg/ml in BBS) was reacted with a 15 fold molar excess of biotin-XX-NHS ester (Molecular Probes, Eugene, Oreg., stock solution at 40 mM in DMSO). The reaction was incubated at room temperature for 90 min and then quenched with taurine (Sigma Chemical Co., St. Louis, Mo.) at a final concentration of 20 mM. The biotinylated reaction mixture was then dialyzed against BBS at 2–8° C. After dialysis, biotinylated SAP was diluted in panning buffer (40 mM Tris, 150 mM NaCl, 20 mg/ml BSA, 0.1% Tween 20, pH 7.5), aliquoted, and stored at −80° C. until needed.

Antibodies were reacted with 3-(N-maleimidylpropionyl) biocytin (Molecular Probes, Eugene, Oreg.) using a free cysteine located at the carboxy terminus of the heavy chain. Antibodies were reduced by adding DTT to a final concentration of 1 mM for 30 min at room temperature. Reduced antibody was passed through a Sephadex G50 desalting column equilibrated in 50 mM potassium phosphate, 10 mM boric acid, 150 mM NaCl, pH 7.0. 3-(N-maleimidylpropionyl)-biocytin was added to a final concentration of 1 mM and the reaction allowed to proceed at room temperature for 60 min. Samples were then dialyzed extensively against BBS and stored at 2–8° C.

Preparation of Avidin Magnetic Latex

The magnetic latex (Estapor, 10% solids, Bangs Laboratories, Fishers, Ind.) was thoroughly resuspended and 2 ml aliquoted into a 15 ml conical tube. The magnetic latex was suspended in 12 ml distilled water and separated from the solution for 10 min using a magnet (PerSeptive Biosystems, Framingham, Mass.). While maintaining the separation of the magnetic latex with the magnet, the liquid was carefully removed using a 10 ml sterile pipette. This washing process was repeated an additional three times. After the final wash, the latex was resuspended in 2 ml of distilled water. In a separate 50 ml conical tube, 10 mg of avidin-HS (NeutrAvidin, Pierce, Rockford, Ill.) was dissolved in 18 ml of 40 mM Tris, 0.15 M sodium chloride, pH 7.5 (TBS). While vortexing, the 2 ml of washed magnetic latex was added to the diluted avidin-HS and the mixture mixed an additional 30 seconds. This mixture was incubated at 45° C. for 2 hr, shaking every 30 minutes. The avidin magnetic latex was separated from the solution using a magnet and washed three times with 20 ml BBS as described above. After the final wash, the latex was resuspended in 10 ml BBS and stored at 4° C.

Immediately prior to use, the avidin magnetic latex was equilibrated in panning buffer (40 mM Tris, 150 mM NaCl, 20 mg/ml BSA, 0.1% Tween 20, pH 7.5). The avidin magnetic latex needed for a panning experiment (200 μl/sample) was added to a sterile 15 ml centrifuge tube and brought to 10 ml with panning buffer. The tube was placed on the magnet for 10 min to separate the latex. The solution was carefully removed with a 10 ml sterile pipette as described above. The magnetic latex was resuspended in 10 ml of panning buffer to begin the second wash. The magnetic latex was washed a total of 3 times with panning buffer. After the final wash, the latex was resuspended in panning buffer to the starting volume.

Example 4

Selection of Recombinant Polyclonal Antibodies to Bacillus Anthracis SAP Antigen Binding reagents that specifically bind to *B. anthracis* SAP were selected from the phage display libraries created from hyperimmunized mice as described in Example 3.

Panning

First round antibody phage were prepared as described in Example 3 using BS45 uracil template. Electroporations of mutagenesis DNA were performed yielding phage samples derived from different immunized mice. To create more diversity in the recombinant polyclonal library, each phage sample was panned separately. Before the first round of functional panning with biotinylated SAP antigen, antibody phage libraries were selected for phage displaying both heavy and light chains on their surface by panning with 7F11-magnetic latex (as described in Examples 21 and 22 of U.S. patent application Ser. No. 08/835,159, filed Apr. 4, 1997). Functional panning of these enriched libraries was performed in principle as described in Example 16 of U.S. patent application Ser. No. 08/835,159. Specifically, 10 μL of $1\times10^{-6}$ M biotinylated SAP antigen was added to the phage samples (approximately $1\times10^{-8}$ M SAP final concentration), and the mixture allowed to come to equilibrium overnight at 2–8° C.

After reaching equilibrium, samples were panned with avidin magnetic latex to capture antibody phage bound to SAP. Equilibrated avidin magnetic latex (Example 3), 200 μL latex per sample, was incubated with the phage for 10 min at room temperature. After 10 min, approximately 9 ml of panning buffer was added to each phage sample, and the magnetic latex separated from the solution using a magnet. After a ten minute separation, unbound phage was carefully removed using a 10 ml sterile pipette. The magnetic latex was then resuspended in 10 ml of panning buffer to begin the second wash. The latex was washed a total of three times as described above. For each wash, the tubes were in contact with the magnet for 10 min to separate unbound phage from the magnetic latex. After the third wash, the magnetic latex was resuspended in 1 ml of panning buffer and transferred to a 1.5 mL tube. The entire volume of magnetic latex for each sample was then collected and resuspended in 200 ul 2×YT and plated on 150 mm LB plates as described in Example 3 to amplify bound phage. Plates were incubated at 37° C. for 4 hr, then overnight at 20° C.

The 150 mm plates used to amplify bound phage were used to generate the next round of antibody phage. After the overnight incubation, second round antibody phage were eluted from the 150 mm plates by pipetting 10 mL of 2×YT media onto the lawn and gently shaking the plate at room temperature for 20 min. The phage samples were then transferred to 15 ml disposable sterile centrifuge tubes with a plug seal cap, and the debris from the LB plate pelleted by centrifuging the tubes for 15 min at 3500 rpm. The supernatant containing the second round antibody phage was then transferred to a new tube.

A second round of functional panning was set up by diluting 100 μL of each phage stock into 900 μL of panning buffer in 15 ml disposable sterile centrifuge tubes. Biotinylated SAP antigen was then added to each sample as described for the first round of panning, and the phage samples incubated for 1 hr at room temperature. The phage samples were then panned with avidin magnetic latex as described above. The progress of panning was monitored at this point by plating aliquots of each latex sample on 100 mm LB agar plates to determine the percentage of kappa positives. The majority of latex from each panning (99%) was plated on 150 mm LB agar plates to amplify the phage bound to the latex. The 100 mm LB agar plates were incubated at 37° C. for 6–7 hr, after which the plates were transferred to room temperature and nitrocellulose filters (pore size 0.45mm, BA85 Protran, Schleicher and Schuell, Keene, N.H.) were overlaid onto the plaques.

Plates with nitrocellulose filters were incubated overnight at room temperature and then developed with a goat anti-mouse kappa alkaline phosphatase conjugate to determine the percentage of kappa positives as described below. Phage samples with lower percentages (<70%) of kappa positives in the population were subjected to a round of panning with 7F 11-magnetic latex before performing a third functional round of panning overnight at 2–8° C. using biotinylated SAP antigen at approximately $2\times10^{-9}$ M. This round of panning was also monitored for kappa positives. Individual phage samples that had kappa positive percentages greater than 80% were pooled and subjected to a final round of panning overnight at 2–8+ C. at $5\times10^{-9}$ M SAP. Antibody genes contained within the eluted phage from this fourth round of functional panning were subcloned into the expression vector, pBRncoH3.

The subcloning process was done generally as described in Example 18 of U.S. patent application Ser. No. 08/835, 159. After subcloning, the expression vector was electroporated into DH10B cells and the mixture grown overnight in 2×YT containing 1% glycerol and 10 μg/ml tetracycline. After a second round of growth and selection in tetracycline, aliquots of cells were frozen at −80° C. as the source for SAP polyclonal antibody production. Two polyclonal antibodies, designated IIT004.1 and IIT005.1, were selected from two libraries derived from different sets of spleens. Monoclonal antibodies were selected from these polyclonal mixtures by plating a sample of the mixture on LB agar plates containing 10 μg/ml tetracycline and screening for antibodies that recognized SAP.

Detection of Alkaline Phosphatase Conjugates

After overnight incubation of nitrocellulose filters on LB agar plates, filters were carefully removed from the plates with membrane forceps and incubated for 2 hr in 10 mM TRIS, 150 mM NaCl, 10 mM $MgCl_2$, 0.1 mM $ZnCl_2$, 0.1% polyvinyl alcohol, 1% bovine serum albumin, 0.1% sodium azide, pH 8.0 (Block buffer). After 2 hr, the filters were incubated with goat anti-mouse kappa-AP (Southern Biotechnology Associates, Inc, Birmingham, Ala.) for 2–4 hours. The goat anti-mouse kappa-AP was diluted into Block buffer at a final concentration of 1 μg/ml. Filters were washed three times with 40 mM Tris, 150 mM NaCl, 0.05% Tween 20, pH 7.5 (TBST) for 5 min each. After the final wash, the filters were developed in a solution containing 0.2 M 2-amino-2-methyl-1-propanol (JBL Scientific, San Luis Obispo, Calif.), 0.5 M Tris, 0.33 mg/ml nitro blue tetrazolium ((NBT) Fisher Scientific, Pittsburgh, Pa.) and 0.166 mg/ml 5-bromo-4-chloro-3-indolyl-phosphate, p-toluidine salt.

Expression and Purification of Recombinant Antibodies Against SAP

A shake flask inoculum was generated overnight from a −70° C. cell bank in an Innova 4330 incubator shaker (New Brunswick Scientific, Edison, N.J.) set at 37° C., 300 rpm. The inoculum was used to seed a 20 L fermentor (Applikon, Foster City, Calif.) containing defined culture medium (Pack et al. (1993) *Bio/Technology* 11: 1271–1277) supplemented with 3 g/L L-leucine, 3 g/L L-isoleucine, 12 g/L casein digest (Difco, Detroit, Mich.), 12.5 g/L glycerol and 10 μg/ml tetracycline. The temperature, pH and dissolved oxygen in the fermentor were controlled at 26° C., 6.0–6.8 and 25% saturation, respectively. Foam was controlled by addition of polypropylene glycol (Dow, Midland, Mich.). Glycerol was added to the fermentor in a fed-batch mode. Fab expression was induced by addition of L(+)-arabinose (Sigma, St. Louis, Mo.) to 2 g/L during the late logarithmic growth phase. Cell density was measured by optical density at 600 nm in an UV-1201 spectrophotometer (Shimadzu, Columbia, Md.). Following run termination and adjustment of pH to 6.0, the culture was passed twice through an M-210B-EH Microfluidizer (Microfluidics, Newton, Mass.) at 17,000 psi. The high pressure homogenization of the cells released the Fab into the culture supernatant.

The first step in purification was expanded bed immobilized metal affinity chromatography (EB-IMAC). Streamline™ chelating resin (Pharmacia, Piscataway, N.J.) was charged with 0.1 M $NiCl_2$ and was then expanded and equilibrated in 50 mM acetate, 200 mM NaCl, 10 mM imidazole, 0.01% $NaN_3$, pH 6.0 buffer flowing in the upward direction. A stock solution was used to bring the culture homogenate to 10 mM imidazole, following which it was diluted two-fold or higher in equilibration buffer to reduce the wet solids content to less than 5% by weight. It was then loaded onto the Streamline column flowing in the upward direction at a superficial velocity of 300 cm/hr. The cell debris passed through unhindered, but the Fab was captured by means of the high affinity interaction between nickel and the hexahistidine tag on the Fab heavy chain. After washing, the expanded bed was converted to a packed bed and the Fab was eluted with 20 mM borate, 150 mM NaCl, 200 mM imidazole, 0.01% $NaN_3$, pH 8.0 buffer flowing in the downward direction.

The second step in the purification used ion-exchange chromatography (IEC). Q Sepharose FastFlow resin (Pharmacia, Piscataway, N.J.) was equilibrated in 20 mM borate, 37.5 mM NaCl, 0.01% $NaN_3$, pH 8.0. The Fab elution pool from the EB-IMAC step was diluted four-fold in 20 mM borate, 0.01% $NaN_3$, pH 8.0 and loaded onto the IEC column. After washing, the Fab was eluted with a 37.5–200 mM NaCl salt gradient. The elution fractions were evaluated for purity using an Xcell II™ SDS-PAGE system (Novex, San Diego, Calif.) prior to pooling. Finally, the Fab pool was concentrated and diafiltered into 20 mM borate, 150 mM NaCl, 0.01% $NaN_3$, pH 8.0 buffer for storage. This was achieved in a Sartocon Slice™ system fitted with a 10,000 MWCO cassette (Sartorius, Bohernia, N.Y.). The final purification yields were typically 50%. The concentration of the purified Fab was measured by UV absorbance at 280 nm, assuming an absorbance of 1.6 for a 1 mg/ml solution.

Culture of *Bacillus* Spp. and Preparation of Cleared Culture Supernatant Antigen Nonencapsulated *Bacillus anthracis*, Sterne strain was obtained from the Colorado Serum Company. *B. cereus* OH599 was the kind gift of Dr. A. Kotiranta, *B. globigii* was obtained from Dr. L. Larson, and *B. thuringiensis* 10792 was obtained from the American Type Culture Collection (Manassas, Va.). Organisms were cultured on tryptic soy agar containing 5% sheep blood (Hardy Diagnostics, Santa Maria, Calif.) or in brain heart infusion broth (Becton Dickinson and Company, Cockeysville, Md.) at 37° C.

For preparation of cleared culture supernatant antigens, *B. anthracis*, Sterne strain was grown in brain heart infusion broth at 37° C. with aeration for 24 h. A sample of the culture was serially diluted 10-fold in sterile 0.01M phosphate buffered saline, pH 7.4 (PBS) and 100 μl of each dilution was plated on a blood agar plate for determination of the number of viable organisms. The culture was subjected to centrifugation at 10,000×g for 20 min at 4° C. using a J2-21 centrifuge (Beclknan, Fullerton, Calif.). The supernatant was transferred to a sterile bottle and a protease inhibitor cocktail (Sigma-Aldrich, Inc) was added. The sample was filtered using a 0.2 μm pore-size membrane filter unit (Millipore Corp., Bedford, Mass.) then dialyzed in 4 L of 0.01M PBS, pH 7.4, 2 mM EDTA, 0.1 mM phenymethylsulfonyl fluoride at 4° C. with four buffer changes in 24 h. The dialyzed sample was aliquoted and stored at −80° C.

The concentration of SAP in the cleared culture supernatant was quantified by a sandwich enzyme-linked immunosorbant assay using purified recombinant SAP as a standard. Analysis of the amount of SAP recovered from the culture supernatant indicated that 1 ng of SAP corresponded to approximately $2.9\times10^3$ organisms (i.e. 0.35 pg/organism).

Example 5

Selection of Monoclonal Antibodies to SAP from the Recombinant Polyclonal Antibody Mixtures Monoclonal antibodies against SAP were isolated from clones containing the recombinant polyclonal mixtures (Example 4) by plating a diluted sample of the mixture on LB agar plates containing 10 μg/ml tetracycline. Individual colonies were then tested for the ability to produce antibody that recognized recombinant SAP using surface plasmon resonance (BIACORE) (BIACORE, Uppsala, Sweden). Small scale production of these monoclonal antibodies was accomplished using a Ni-chelate batch-binding method (see below). Antibodies isolated from this method were diluted 1:3 in HBS-EP (0.01 M HEPES, pH 7.4, 0.15 M NaCl, 3 mM EDTA, 0.005% polysorbate 20 (v/v)), captured with a goat anti-mouse kappa antibody (Southern Biotechnology Associates, Inc, Birmingham, Ala.) coupled to a BIACORE CM5 sensor chip, and tested for the ability to bind recombinant SAP. Antibodies that bound SAP were then evaluated using BIACORE epitope mapping analysis. Antibodies that bound distinct epitopes were produced on a larger scale and then conjugated to biotin and alkaLine phosphatase. These conjugates were then tested in an ELISA assay to determine the sensitivity and utility of these antibodies.

Minipreparation of Monoclonal Antibodies by Ni-chelate Batch-bindine Method

Individual colonies were isolated from the recombinant polyclonal mixtures (Example 4) and used to inoculate 3 ml cultures of 2×YT medium containing 1% glycerol supplemented with 10 μg/ml tetracycline. These cultures were grown in an Innova 4330 incubator shaker (New Brunswick Scientific, Edison, N.J.) set at 37° C., 300 rpm. The next morning 0.5 ml of each culture was used to inoculate shake flasks containing 50 ml of defined medium, (Pack et al. (1993) *Bio/Technology* 11: 1271–1277) supplemented with 3 g/L L-leucine, 3 g/L L-isoleucine, 12 g/L casein digest (Difco, Detroit, Mich.), 12.5 μg/L glycerol and 10 μg/ml tetracycline. These cultures were shaken at 300 rpm, 37° C. until an optical density of 4 was reached at 600 nm. Fab expression was then induced by adding L(+)-arabinose (Sigma, St. Louis, Mo.) to 2 g/L and shifting the temperature to 23° C. with overnight shaking. The next day the following was added to the 50 ml cultures: 0.55 ml of 1 M imidazole, 5 ml B-PER (Pierce, Rockford, Ill.) and 2 ml Ni-chelating resin (Chelating Sepharose FastFlow™ resin Pharmacia, Piscataway, N.J.). The mixture was shaken at 300 rpm, 23° C. for 1 hour after which time shaking was stopped and the resin allowed to settle to the bottom of the flasks for 15 minutes.

The supernatant was then poured off and the resin resuspended in 40 ml of BBS (20 mM borate, 150 mM NaCl, 0.1% $NaN_3$, pH 8.0) containing 10 mM imidazole. This suspension was transferred to a 50 ml conical tube and the resin washed a total of 3 times with BBS containing 10 mM imidazole. Washing was accomplished by low speed centrifugation (1100 rpm for 1 minute), removal of supernatant and, resuspension of the resin in BBS containing 10 mM imidazole. After the supernatant of the final wash was poured off, 0.5 ml of 1 M imidazole was added to each tube, vortex briefly, and transferred to a sterile microcentrifuge tube. The samples were then centrifuged at 14 krpm for 1 minutes and the supernatant transferred to a new microcentrifuge tube. Antibodies contained in the supernatant were then analyzed for binding to SAP using a BIACORE (BIACORE, Uppsala, Sweden).

Selection and Cloning of a Recombinant Polyclonal Antibody Complementary to IIT005.1.13 and IIT005.1.C.11 Monoclonal Antibodies A monoclonal antibody designated IIT004.1.12 was selected from the polyclonal library designated IIT004.1, biotinylated, and 15 μl of a $10^{-6}$ M solution was mixed with soluble recombinant SAP antigen (7.5 μl of a $10^{-7}$ M solution). This mixture was incubated for 15 minutes at room temperature. Fifteen microliters of each mixture was added to 50 μl of phage library IIT005.1 diluted in 1 ml panning buffer (40 mM Tris, 150 mM NaCl, 20 mg/ml BSA, 0.1% Tween 20, pH 7.5) and incubated overnight at 2–8° C. Final concentrations were $10^{-8}$M biotinylated monoclonal antibody and $5\times10^{-10}$ M SAP. The sample was panned with avidin magnetic latex and plated as described in Example 4. The eluted phage were subjected to another round of selection using these conditions and the resulting polyclonal library was designated IIT005.1.C. Two monoclonal antibodies designated IIT005.1.13 and IIT005.1.C.11 were selected from the IIT005.1 and IIT005.1.C libraries respectively, biotinylated and complexed with SAP using the conditions described above. Complementary polyclonal antibodies were selected as described above from phage library IIT005.1 using monoclonal antibodies IIT005.1.13 and IIT005.1.C.11. These complementary polyclona antibodies were designated IIT005.1.13.1 and IIT005.1.C.11.1 and were subcloned as described in Example 18 of U.S. patent application Ser. No. 08/835,159.

Example 6

Specificity of Monoclonal/Polyclonal Antibodies to SAP Determined by Western Blot and Indirect Immunofluorescence Analysis The specificity of monoclonal and polyclonal antibodies against *B. anthracis*, Sterne strain SAP was visualized by Western blot analysis. Recombinant antibodies against SAP were tested for reactivity to recombinant SAP as well as to SAP isolated from the cleared culture supernatant of *Bacillus anthracis* Steme strain. Cross reactivity to other Bacillus strains was also tested. Culture supernatant proteins and whole cell lysates of *B. anthracis*, Sterne strain, *B. cereus* OH599, *B. globigii* and *B. thuringiensis* 10792 equivalent to $10^8$ organisms were separated by electrophoresis in 4–20% TRIS-glycine SDS-polyacrylamide gels (Novex, San Diego, Calif.) under reducing conditions. The proteins were transferred to ProBlott™ membranes (Applied Biosystems, Foster City, Calif.) using 10 mM CAPS/10% methanol transfer buffer. The membranes were blocked in 10 mM TRIS, 150 mM NaCl, 10 mM $MgCl_2$, 0.1 mM $ZnCl_2$, 0.1% polyvinyl alcohol, 1% bovine serum albumin, 0.1% sodium azide, pH 8.0 (Block buffer) for 1 h at room temperature.

The membranes were then incubated in 5 μg/ml of monoclonal or recombinant polyclonal antibody diluted in Block buffer for 1 h and then washed three times with 40 mM TRIS, 150 mM NaCl, 0.05% Tween 20, pH 7.5 (TBST) (Fisher Chemical, Pittsburgh, Pa.) for 5 min each. After washing, the membranes were incubated in rabbit anti-mouse IgG (H&L)-alkaline phosphatase conjugate (Southern Biotechnology, Inc, Birmingham, Ala.) diluted 1:1000 in Block buffer. The membranes were washed three times with TBST for 5 min each and developed in a solution containing 0.2 M 2-amino-2-methyl-1-propanol (JBL Scientific, San Luis Obispo, Calif.), 0.5 M TRIS, 0.33 mg/ml nitro blue tetrazolium ((NBT) Fisher Scientific, Pittsburgh, Pa.) and 0.166 mg/ml 5-bromo-4-chloro-3-indolyl-phosphate, p-toluidine salt.

The anti-SAP recombinant polyclonal antibodies reacted with recombinant SAP, SAP protein isolated from the culture supernatant, and the cell pellet of *B. anthracis*, Sterne strain. The antibodies did not react with any proteins in the culture supernatant or cell pellet of the other Bacillus species tested (*B. cereus* and *thuringiensis*). A goat anti-anthrax polyclonal serum was used to demonstrate cross-reactivity of *B. anthracis* antibodies with proteins of other Bacillus species (data not shown). Conjugates alone served as negative controls.

The specificity of antibodies against *B. anthracis*, Sterne strain was also tested by indirect immunofluorescence. Localization of SAP to the outer membrane of unencapsulated *B. anthracis*, Sterne strain was demonstrated using an indirect immunofluorescence technique. *B. anthracis, B. cereus*, and *B. thuringiensis* were washed and resuspended in PBS to yield $1\times10^8$ organisms per ml. Four microliters of the suspensions were applied to wells of an eight well microscope slide and allowed to air dry. The slides were lightly heated to fix the smears to the slide and covered with 0.1 mg/ml of antibody diluted in PBS containing 1% BSA. The smears were incubated with antibody for 1 h at 37° C. in a moist chamber. After washing the slides three times by soaking in PBS for 5 min each, the smears were covered with fluorescein isothiocyanate-conjugated rabbit anti-mouse IgG (H&L) $F(ab')_2$ (Zymed Laboratories, Inc., South San Francisco, Calif.) diluted 1:80 in PBS, 1% BSA, 0.05% Evans Blue (Sigma). The slides were incubated for 1 h at 37° C. in a moist chamber then washed as described above. After a final wash in deionized water, the slides were allowed to air dry in the dark. Coverslips were mounted using a 90% glycerol mounting medium containing 10 mg/ml p-phenylenediamine, pH 8.0.

The slides were examined for fluorescent organisms using an epifluorescence microscope with a 63× objective lens (Leitz Wetzler Germany). The recombinant polyclonal antibody (ITT005.1) demonstrated 4+ fluorescence with unencapsulated *B. anthracis* and did not react with *B. cereus*, or *B. thuringiensis*. Negative controls included fluorescein-conjugated antibody alone, and a murine polyclonal antiserum specific for *B. anthracis*, Sterne strain spore coat proteins.

Example 7

Sensitivity and Specificity of an ELISA Plate Assay for Detection of *B. anthracis* SAP This Example demonstrates that an ELISA assay using the reagents and methods of the invention are not only highly sensitive for *B. anthracis*, but are also highly specific for this particular *Bacillus* species.

The sensitivity and specificity of various monoclonal/recombinant polyclonal antibody pairs were determined by performing a sandwich assay using biotinylated monoclonal antibodies and alkaline phosphatase-conjugated recombinant polyclonal antibodies. Assays were performed with NeutraAvidin or streptavidin coated plates, such as Reacti-Bind™ streptavidin coated polystyrene 96 well plates (Pierce Chemical, Rockford, Ill.). After washing the 96 well plate with BBS (20 mM borate, 150 mM NaCl, 0.01% $NaN_3$, pH 8.0) containing 0.02% TWEEN-20, biotinylated monoclonal antibodies (50 $\mu$L of 2.5 $\mu$g/mL diluted in Block buffer (10 mM Tris, 150 mM NaCl, 10 mM $MgCl_2$, 0.1 mM $ZnCl_2$, 0.1% polyvinyl alcohol, 1% bovine serum albumin, 0.1% sodium azide, pH 8.0)) were added to the wells. The plate was incubated at room temperature for 1 hr.

The plate was then washed, after which various dilutions (10 ng/ml to 0.625 ng/ml) of soluble SAP antigen (50 $\mu$L of recombinant SAP or SAP in culture supernatants (as prepared in Example 4) were added in duplicate to the biotinylated monoclonal wells. The plates were incubated for one hour at room temperature or overnight at 2–8° C., after which the plate was washed. The appropriate recombinant polyclonal antibody-alkaline phosphatase conjugate (50 $\mu$L of 2.5 $\mu$g/mL diluted in Block) was added and incubated at room temperature for 1 hr. After 1 hr, the plate was washed and developed using the ELISA Amplification System (Gibco BRL, Gaithersburg, Md.) according to the manufacturer's instructions.

Results from several assays are compiled in accompanying tables 2–5. These data indicate that the assays can detect less than 0.625 ng of SAP protein. This amount of SAP corresponds to approximately $1.8\times10^3$ *Bacillus anthracis* organisrns per ml. Significantly, little or no cross reactivity to other related Bacillus species was detected.

TABLE 2

IIT005.1.C.11-BIOTIN WITH IIT005.1.C11.1-AP

| *B. anthracis* culture (cfu/ml) | A490 | SAP (ng/mL) | A490 | Undiluted Bacillus species | A490 |
|---|---|---|---|---|---|
| 28330 | 3.4 | 10 | 3.55 | *cereus* | 0.28 |
| 14165 | 2.8 | 5 | 3.45 | *thuringiensis* | 0.27 |
| 7083 | 2.14 | 2.5 | 2.94 | *subtilis niger* | 0.55 |
| 3541 | 1.56 | 1.25 | 2.01 | *subtilis* | 0.51 |
| 1770 | 1.17 | 0.625 | 1.51 | BHI broth | 0.48 |
| 0 | 0.92 | 0 | 0.92 | media | |

TABLE 3

IIT005.1.13-BIOTIN WITH IIT005.1.13.1-AP

| *B. anthracis* culture (cfu/ml) | A490 | Undiluted Bacillus species | A490 |
|---|---|---|---|
| 28330 | 3.13 | *cereus* | 0.28 |
| 14165 | 2.21 | *thuringiensis* | 0.27 |
| 7083 | 1.5 | *subtilis niger* | 0.48 |
| 3541 | 0.99 | *subtilis* | 0.5 |
| 1770 | 0.78 | BHI broth | 0.423 |
| 0 | 0.55 | media | |

TABLE 4

IIT005.1.C.11-BIOTIN WITH IIT005.1-AP

| *B. anthracis* culture (cfu/ml) | A490 | SAP (ng/mL) | A490 | Undiluted Bacillus species | A490 |
|---|---|---|---|---|---|
| 28330 | 2.87 | 10 | 3.4 | *cereus* | 0.09 |
| 14165 | 1.698 | 5 | 2.56 | *thuringiensis* | 0.14 |
| 7083 | 1 | 2.5 | 1.49 | *subtilis niger* | 0.13 |
| 3541 | 0.55 | 1.25 | 0.82 | *subtilis* | 0.14 |

TABLE 4-continued

IIT005.1.C.11-BIOTIN WITH IIT005.1-AP

| *B. anthracis* culture (cfu/ml) | A490 | SAP (ng/mL) | A490 | Undiluted Bacillus species | A490 |
|---|---|---|---|---|---|
| 1770 | 0.35 | 0.625 | 0.49 | BHI broth | 0.148 |
| 0 | 0.14 | 0 | 0.19 | media | |

TABLE 5

IIT005.1.13-BIOTIN WITH IIT005.1-AP

| *B. anthracis* culture (cfu/ml) | A490 | Undiluted Bacillus species | A490 |
|---|---|---|---|
| 28330 | 1.77 | *cereus* | 0.085 |
| 14165 | 0.99 | *thuringiensis* | 0.121 |
| 7083 | 0.54 | *subtilis niger* | 0.125 |
| 3541 | 0.34 | *subtilis* | 0.124 |

TABLE 5-continued

IIT005.1.13-BIOTIN WITH IIT005.1-AP

| *B. anthracis* culture (cfu/ml) | A490 | Undiluted Bacillus species | A490 |
|---|---|---|---|
| 1770 | 0.23 | BHI broth | 0.125 |
| 0 | 0.14 | media | |

These results demonstrate that four different monoclonal/recombinant polyclonal antibody preparations exhibit great sensitivity for *B. anthracis* while not cross reacting with other *Bacillus* species.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A method of specifically detecting the *Bacillus anthracis* surface array protein SEQ ID NO:1 in a test sample, the method comprising:

contacting a test sample with a first antibody that specifically binds to *Bacillus anthracis* surface array protein as set forth in SEQ ID NO:1, wherein the first antibody forms a complex with the surface array protein but does not form a complex with protein from non-*anthracis Bacillus* species present in the test sample; and detecting the complex with a labeled second antibody that binds to the complex, wherein the detection of the complex is indicative of the presence of *Bacillus anthracis* in the test sample.

2. The method of claim 1, wherein the *B. anthracis* present in the test sample is encapsulated.

3. The method of claim 1, wherein the first or second antibody is a recombinantly produced antibody.

4. The method of claim 3, wherein the first or second antibody is a recombinantly produced polyclonal antibody.

5. The method of claim 1, wherein the first or second antibody is monoclonal antibody.

6. The method of claim 1, wherein the test sample is collected from a site of suspected or threatened anthrax contamination.

7. The method of claim 6, wherein the test sample is collected using a cyclonic collection device.

8. The method of claim 1, wherein the test sample is not cultured prior to contacting with the first antibody.

9. The method of claim 1, wherein the first antibody is immobilized on a solid support.

10. The method of claim 9, wherein the solid support is a microtiter dish.

11. The method of claim 9, wherein the first antibody is immobilized on the solid support prior to contacting the first antibody with the test sample.

12. The method of claim 1, wherein the method can detect *B. anthracis* at concentrations as low as about 10,000 cfu/ml.

13. The method of claim 12, wherein the method can detect *B. anthracis* at concentrations as low as about 5,000 cfu/ml.

14. The method of claim 13, wherein the method can detect *B. anthracis* at concentrations as low as about 1,800 cfu/ml.

15. The method of claim 1, wherein the second antibody binds to a different epitope of the surface array protein than does the first antibody.

16. The method of claim 1, wherein the label of the labeled second antibody is selected from the group consisting of a radioactive label, a fluorophore, a dye, an enzyme, and a chemiluminescent label.

17. A kit for detecting the presence or absence of *Bacillus anthracis* in a sample, the kit comprising:

a first antibody that specifically binds to the surface array protein set forth in SEQ ID NO:1 but does not bind to protein from non-*anthracis Bacillus* species; and a label.

18. The kit of claim 17, wherein the first antibody is a recombinant polyclonal antibody.

19. The kit of claim 17, wherein the first antibody is a monoclonal

20. The kit of claim 17, wherein the first antibody is a mixture of monoclonal and polyclonal antibody preparations.

21. The kit of claim 17, wherein the kit further comprises written instructions for using the kit to determine whether a test sample contains *B. anthracis.*.

22. The kit according to claim 17, wherein the kit further comprises a positive control that comprises a polypeptide that comprises an antigenic determinant of a *B. anthracis* surface array protein, wherein the antigenic determinant binds to said first antibody.

23. The kit of claim 17, wherein the kit further comprises a second antibody which binds the surface array protein as set forth in SEQ ID NO:1.

24. The kit of claim 17, wherein the first antibody is immobilized on a solid support.

25. The kit of claim 23, wherein the second antibody is a recombinant polyclonal antibody.

26. The kit of claim 23, wherein the second antibody is a monoclonal antibody.

27. The kit of claim 23, wherein the second antibody is a mixture of monoclonal and polyclonal antibody preparations.

28. The kit of claim 24, wherein the solid support is a microtiter dish.

* * * * *

SEQUENCE LISTING

<160> NUMBER OF SEQ ID NOS: 5

<210> SEQ ID NO 1
<211> LENGTH: 785
<212> TYPE: PRT
<213> ORGANISM: Bacillus anthracis
<220> FEATURE:
<223> OTHER INFORMATION: surface array protein (SAP)

<400> SEQUENCE: 1

Ala Gly Lys Thr Phe Pro Asp Val Pro Ala Asp His Trp Gly Ile Asp
1               5                   10                  15

Ser Ile Asn Tyr Leu Val Glu Lys Gly Ala Val Lys Gly Asn Asp Lys
            20                  25                  30

Gly Met Phe Glu Pro Gly Lys Glu Leu Thr Arg Ala Glu Ala Ala Thr
        35                  40                  45

Met Met Ala Gln Ile Leu Asn Leu Pro Ile Asp Lys Asp Ala Lys Pro
    50                  55                  60

Ser Phe Ala Asp Ser Gln Gly Gln Trp Tyr Thr Pro Phe Ile Ala Ala
65                  70                  75                  80

Val Glu Lys Ala Gly Val Ile Lys Gly Thr Gly Asn Gly Phe Glu Pro
                85                  90                  95

Asn Gly Lys Ile Asp Arg Val Ser Met Ala Ser Leu Leu Val Glu Ala
            100                 105                 110

Tyr Lys Leu Asp Thr Lys Val Asn Gly Thr Pro Ala Thr Lys Phe Lys
        115                 120                 125

Asp Leu Glu Thr Leu Asn Trp Gly Lys Glu Lys Ala Asn Ile Leu Val
    130                 135                 140

Glu Leu Gly Ile Ser Val Gly Thr Gly Asp Gln Trp Glu Pro Lys Lys
145                 150                 155                 160

-continued

```
Thr Val Thr Lys Ala Glu Ala Ala Gln Phe Ile Ala Lys Thr Asp Lys
                165                 170                 175

Gln Phe Gly Thr Glu Ala Ala Lys Val Glu Ser Ala Lys Ala Val Thr
            180                 185                 190

Thr Gln Lys Val Glu Val Lys Phe Ser Lys Ala Val Glu Lys Leu Thr
        195                 200                 205

Lys Glu Asp Ile Lys Val Thr Asn Lys Ala Asn Asn Asp Lys Val Leu
    210                 215                 220

Val Lys Glu Val Thr Leu Ser Glu Asp Lys Arg Ser Ala Thr Val Glu
225                 230                 235                 240

Leu Tyr Ser Asn Leu Ala Ala Lys Gln Thr Tyr Thr Val Asp Val Asn
                245                 250                 255

Lys Val Gly Lys Thr Glu Val Ala Val Gly Ser Leu Glu Ala Lys Thr
            260                 265                 270

Ile Glu Met Ala Asp Gln Thr Val Val Ala Asp Glu Pro Thr Ala Leu
        275                 280                 285

Gln Phe Thr Val Lys Asp Glu Asn Gly Thr Glu Val Val Ser Pro Glu
    290                 295                 300

Gly Ile Glu Phe Val Thr Pro Ala Ala Glu Lys Ile Asn Ala Lys Gly
305                 310                 315                 320

Glu Ile Thr Leu Ala Lys Gly Thr Ser Thr Thr Val Lys Ala Val Tyr
                325                 330                 335

Lys Lys Asp Gly Lys Val Val Ala Glu Ser Lys Glu Val Lys Val Ser
            340                 345                 350

Ala Glu Gly Ala Ala Val Ala Ser Ile Ser Asn Trp Thr Val Ala Glu
        355                 360                 365

Gln Asn Lys Ala Asp Phe Thr Ser Lys Asp Phe Lys Gln Asn Asn Lys
    370                 375                 380

Val Tyr Glu Gly Asp Asn Ala Tyr Val Gln Val Glu Leu Lys Asp Gln
385                 390                 395                 400

Phe Asn Ala Val Thr Thr Gly Lys Val Glu Tyr Glu Ser Leu Asn Thr
                405                 410                 415

Glu Val Ala Val Val Asp Lys Ala Thr Gly Lys Val Thr Val Leu Ser
            420                 425                 430

Ala Gly Lys Ala Pro Val Lys Val Thr Val Lys Asp Ser Lys Gly Lys
        435                 440                 445

Ala Leu Val Ser His Thr Val Glu Ile Glu Ala Phe Ala Gln Lys Ala
    450                 455                 460

Met Lys Asp Ile Lys Leu Glu Lys Thr Asn Val Ala Leu Ser Thr Lys
465                 470                 475                 480

Asp Val Thr Asp Leu Lys Val Lys Ala Pro Val Leu Asp Gln Tyr Gly
                485                 490                 495

Lys Glu Phe Thr Ala Pro Val Thr Val Lys Val Leu Asp Lys Asp Gly
            500                 505                 510

Lys Glu Leu Lys Glu Gln Lys Leu Glu Ala Lys Tyr Val Asn Arg Glu
        515                 520                 525

Leu Val Leu Asn Ala Ala Gly Gln Glu Ala Gly Asn Tyr Thr Val Val
    530                 535                 540

Leu Thr Ala Lys Ser Gly Glu Lys Glu Ala Lys Ala Thr Leu Ala Leu
545                 550                 555                 560

Glu Leu Lys Ala Pro Gly Ala Phe Ser Lys Phe Glu Val Arg Gly Leu
                565                 570                 575

Asp Thr Glu Leu Asp Lys Tyr Val Thr Glu Glu Asn Gln Lys Asn Ala
```

-continued

```
            580                 585                 590

Met Thr Val Ser Val Leu Pro Val Asp Ala Asn Gly Leu Val Leu Lys
        595                 600                 605

Gly Ala Glu Ala Ala Glu Leu Lys Val Thr Thr Thr Asn Lys Glu Gly
    610                 615                 620

Lys Glu Val Asp Ala Thr Asp Ala Gln Val Thr Val Gln Asn Asn Ser
625                 630                 635                 640

Val Ile Thr Val Gly Gln Gly Ala Lys Ala Gly Glu Thr Tyr Lys Val
                645                 650                 655

Thr Val Val Leu Asp Gly Lys Leu Ile Thr Thr His Ser Phe Lys Val
            660                 665                 670

Val Asp Thr Ala Pro Thr Ala Lys Gly Leu Ala Val Glu Phe Thr Ser
        675                 680                 685

Thr Ser Leu Lys Glu Val Ala Pro Asn Ala Asp Leu Lys Ala Ala Leu
    690                 695                 700

Leu Asn Ile Leu Ser Val Asp Gly Val Pro Ala Thr Thr Ala Lys Ala
705                 710                 715                 720

Thr Ala Ser Asn Val Glu Phe Val Ser Ala Asp Thr Asn Val Val Ala
                725                 730                 735

Glu Asn Gly Thr Val Gly Ala Lys Gly Ala Thr Ser Ile Tyr Val Lys
            740                 745                 750

Asn Leu Thr Val Val Lys Asp Gly Lys Glu Gln Lys Val Glu Phe Asp
        755                 760                 765

Lys Ala Val Gln Val Ala Val Ser Ile Lys Glu Ala Lys Pro Ala Thr
    770                 775                 780

Lys
785


<210> SEQ ID NO 2
<211> LENGTH: 2370
<212> TYPE: DNA
<213> ORGANISM: Bacillus anthracis
<220> FEATURE:
<223> OTHER INFORMATION: surface array protein (SAP)

<400> SEQUENCE: 2

aaaacattcc cagacgttcc tgctgatcac tggggaattg attccattaa ctacttagta     60

gaaaaaggcg cagttaaagg taacgacaaa ggaatgttcg agcctggaaa agaattaact    120

cgtgcagaag cagctacaat gatggctcaa atcttaaact taccaatcga taaagatgct    180

aaaccatctt tcgctgactc tcaaggccaa tggtacactc cattcatcgc agctgtagaa    240

aaagctggcg ttattaaagg tacaggaaac ggctttgagc caaacggaaa aatcgaccgc    300

gtttctatgg catctcttct tgtagaagct tacaaattag atactaaagt aaacggtact    360

ccagcaacta aattcaaaga tttagaaaca ttaaactggg gtaaagaaaa agctaacatc    420

ttagttgaat taggaatctc tgttggtact ggtgatcaat gggagcctaa gaaaactgta    480

actaaagcag aagctgctca attcattgct aagactgaca agcagttcgg tacagaagca    540

gcaaaagttg aatctgcaaa agctgttaca actcaaaaag tagaagttaa attcagcaaa    600

gctgttgaaa aattaactaa agaagatatc aaagtaacta acaaagctaa caacgataaa    660

gtactagtta aagaggtaac tttatcagaa gataaaagat ctgctacagt tgaattatat    720

agtaacttag cagctaaaca aacttacact gtagatgtaa acaaagttgg taaaacagaa    780

gtagctgtag gttctttaga agcaaaaaca atcgaaatgg ctgaccaaac agttgtagct    840
```

-continued

```
gatgagccaa cagcattaca attcacagtt aaagatgaaa acggtactga agttgtttca    900

ccagagggta ttgaatttgt aacgccagct gcagaaaaaa ttaatgcaaa aggtgaaatc    960

actttagcaa aggtacttc aactactgta aaagctgttt ataaaaaaga cggtaaagta   1020

gtagctgaaa gtaaagaagt aaaagtttct gctgaaggtg ctgcagtagc ttcaatctct   1080

aactggacag ttgcagaaca aaataaagct gactttactt ctaaagattt caaacaaaac   1140

aataaagttt acgaaggcga caacgcttac gttcaagtag aattgaaaga tcaatttaac   1200

gcagtaacaa ctggaaaagt tgaatatgag tcgttaaaca cagaagttgc tgtagtagat   1260

aaagctactg gtaaagtaac tgtattatct gcaggaaaag caccagtaaa agtaactgta   1320

aaagattcaa aaggtaaagc acttgtttca cacacagttg aaattgaagc tttcgctcaa   1380

aaagcaatga aagacattaa attagaaaaa actaacgtag cgctttctac aaaagatgta   1440

acagatttaa aagtaaaagc tccagtacta gatcaatacg gtaaagagtt tacagctcct   1500

gtaacagtga aagtacttga taaagatggt aaagaattaa aagaacaaaa attagaagct   1560

aaatatgtga acagagaatt agttctgaat gcagcaggtc aagaagctgg taattataca   1620

gttgtattaa ctgcaaaatc tggtgaaaaa gaagcaaaag ctacattagc tctagaatta   1680

aaagctccag gtgcattctc taaatttgaa gttcgtggtt tagacacaga attagataaa   1740

tatgttactg aggaaaacca aaagaatgca atgactgttt cagttcttcc tgtagatgca   1800

aatggattag tattaaaagg tgcagaagca gctgaactaa aagtaacaac aacaaacaaa   1860

gaaggtaaag aagtagacgc aactgatgca caagttactg tacaaaataa cagtgtaatt   1920

actgttggtc aaggtgcaaa agctggtgag acttataaag taacagttgt actagatggt   1980

aaattaatca caactcattc attcaaagtt gttgatacag caccaactgc taaaggatta   2040

gcagtagaat ttacaagcac atctcttaaa gaagtagctc caaatgctga tttaaaagct   2100

gcacttttaa atatcttatc tgttgatggt gtacctgcga ctacagcaaa agcaacagct   2160

tctaatgtag aatttgtttc tgctgacaca aatgttgtag ctgaaaatgg tacagttggt   2220

gcaaaaggtg caacatctat ctatgtgaaa aacctgacag ttgtaaaaga tggaaaagag   2280

caaaaagtag aatttgataa agctgtacaa gttgcagttt ctattaaaga agcaaaacct   2340

gcaacaaaac atcaccatca ccatcactaa                                    2370
```

<210> SEQ ID NO 3
<211> LENGTH: 44
<212> TYPE: DNA
<213> ORGANISM: Artificial Sequence
<220> FEATURE:
<223> OTHER INFORMATION: Description of Artificial Sequence:5' PCR primer

<400> SEQUENCE: 3

```
tcgctgccca accagccatg gccgcaggta aaacattccc agac                      44
```

<210> SEQ ID NO 4
<211> LENGTH: 89
<212> TYPE: DNA
<213> ORGANISM: Artificial Sequence
<220> FEATURE:
<223> OTHER INFORMATION: Description of Artificial Sequence:3' PCR primer

<400> SEQUENCE: 4

```
gtgataaact accgcattaa agcttatcga tgataagctg tcaattagtg atggtgatgg     60

tgatgttttg ttgcaggttt tgcttcttt                                       89
```

-continued

```
<210> SEQ ID NO 5
<211> LENGTH: 201
<212> TYPE: PRT
<213> ORGANISM: Artificial Sequence
<220> FEATURE:
<223> OTHER INFORMATION: Description of Artificial Sequence:flexible
      linker
<221> NAME/KEY: MOD_RES
<222> LOCATION: (1)..(97)
<223> OTHER INFORMATION: Gly at positions 1-97 may be present or absent
<221> NAME/KEY: MOD_RES
<222> LOCATION: (105)..(201)
<223> OTHER INFORMATION: Gly at positions 105-201 may be present or
      absent

<400> SEQUENCE: 5

Gly Gly Gly Gly Gly Gly Gly Gly Gly Gly Gly Gly Gly Gly Gly Gly
  1               5                  10                  15

Gly Gly Gly Gly Gly Gly Gly Gly Gly Gly Gly Gly Gly Gly Gly Gly
             20                  25                  30

Gly Gly Gly Gly Gly Gly Gly Gly Gly Gly Gly Gly Gly Gly Gly Gly
         35                  40                  45

Gly Gly Gly Gly Gly Gly Gly Gly Gly Gly Gly Gly Gly Gly Gly Gly
     50                  55                  60

Gly Gly Gly Gly Gly Gly Gly Gly Gly Gly Gly Gly Gly Gly Gly Gly
 65                  70                  75                  80

Gly Gly Gly Gly Gly Gly Gly Gly Gly Gly Gly Gly Gly Gly Gly Gly
                 85                  90                  95

Gly Gly Gly Gly Pro Gly Gly Gly Gly Gly Gly Gly Gly Gly Gly Gly
            100                 105                 110

Gly Gly Gly Gly Gly Gly Gly Gly Gly Gly Gly Gly Gly Gly Gly Gly
        115                 120                 125

Gly Gly Gly Gly Gly Gly Gly Gly Gly Gly Gly Gly Gly Gly Gly Gly
    130                 135                 140

Gly Gly Gly Gly Gly Gly Gly Gly Gly Gly Gly Gly Gly Gly Gly Gly
145                 150                 155                 160

Gly Gly Gly Gly Gly Gly Gly Gly Gly Gly Gly Gly Gly Gly Gly Gly
                165                 170                 175

Gly Gly Gly Gly Gly Gly Gly Gly Gly Gly Gly Gly Gly Gly Gly Gly
            180                 185                 190

Gly Gly Gly Gly Gly Gly Gly Gly Gly
        195                 200
```